(12) United States Patent
Makin et al.

(10) Patent No.: US 8,282,554 B2
(45) Date of Patent: Oct. 9, 2012

(54) METHODS FOR TREATMENT OF SWEAT GLANDS

(75) Inventors: Inder Raj S. Makin, Mesa, AZ (US);
Peter G. Barthe, Phoenix, AZ (US);
Michael H. Slayton, Tempe, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 0 days.

(21) Appl. No.: 13/444,485

(22) Filed: Apr. 11, 2012

(65) Prior Publication Data

US 2012/0197120 A1     Aug. 2, 2012

Related U.S. Application Data

(63) Continuation of application No. 11/163,152, filed on Oct. 6, 2005, now abandoned.

(60) Provisional application No. 60/616,752, filed on Oct. 6, 2004.

(51) Int. Cl.
*A61N 7/02* (2006.01)
(52) U.S. Cl. .................................. 600/439; 600/437
(58) Field of Classification Search .......... 600/437–439; 606/27, 41; 128/898
See application file for complete search history.

(56) References Cited

U.S. PATENT DOCUMENTS

| | | | |
|---|---|---|---|
| 2,427,348 A | 9/1947 | Bond et al. |
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,381,007 A | 4/1983 | Doss |

(Continued)

FOREIGN PATENT DOCUMENTS

DE     4029175     3/1992

(Continued)

OTHER PUBLICATIONS

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

(Continued)

*Primary Examiner* — Michael Peffley
*Assistant Examiner* — Ronald Hupczey, Jr.
(74) *Attorney, Agent, or Firm* — Knobbe Martens Olson & Bear LLP

(57) ABSTRACT

A method and system for ultrasound treatment of sweat glands are provided. An exemplary method and system for targeted treatment of sweat glands can be configured in various manners, such as through use of therapy only, therapy and monitoring, imaging and therapy, or therapy, imaging, and monitoring, and/or through use of focused, unfocused, or defocused ultrasound through control of various spatial and temporal parameters. As a result, ablative energy can be deposited at the particular depth at which the aberrant sweat gland population is located below the skin surface.

20 Claims, 20 Drawing Sheets

U.S. PATENT DOCUMENTS

| | | |
|---|---|---|
| 4,381,787 A | 5/1983 | Hottinger |
| 4,397,314 A | 8/1983 | Vaguine |
| 4,409,839 A | 10/1983 | Tanezer |
| 4,441,486 A | 4/1984 | Pounds |
| 4,452,084 A | 6/1984 | Taenzer |
| 4,484,569 A | 11/1984 | Driller |
| 4,513,749 A | 4/1985 | Kino |
| 4,527,550 A | 7/1985 | Ruggera et al. |
| 4,528,979 A | 7/1985 | Marchenko |
| 4,567,895 A | 2/1986 | Putzke |
| 4,586,512 A | 5/1986 | Do-Huu |
| 4,601,296 A | 7/1986 | Yerushalmi |
| 4,646,756 A | 3/1987 | Watmough |
| 4,663,358 A | 5/1987 | Hyon |
| 4,668,516 A | 5/1987 | Duraffourd et al. |
| 4,697,588 A | 10/1987 | Reichenberger |
| 4,757,820 A | 7/1988 | Itoh |
| 4,807,633 A | 2/1989 | Fry |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,893,624 A | 1/1990 | Lele |
| 4,896,673 A | 1/1990 | Rose |
| D306,965 S | 4/1990 | Jaworski |
| 4,917,096 A | 4/1990 | Englehart |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 5,012,797 A | 5/1991 | Liang |
| 5,036,855 A | 8/1991 | Fry |
| 5,054,470 A | 10/1991 | Fry |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,150,711 A | 9/1992 | Dory |
| 5,150,714 A | 9/1992 | Green |
| 5,156,144 A | 10/1992 | Iwasaki |
| 5,158,536 A | 10/1992 | Sekins |
| 5,163,421 A | 11/1992 | Bernstein |
| 5,191,880 A | 3/1993 | McLeod |
| 5,209,720 A | 5/1993 | Unger |
| 5,224,467 A | 7/1993 | Oku |
| 5,230,334 A | 7/1993 | Klopotek |
| 5,230,338 A | 7/1993 | Allen et al. |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus |
| 5,304,169 A | 4/1994 | Sand |
| 5,321,520 A | 6/1994 | Inga et al. |
| 5,360,268 A | 11/1994 | Hayashi |
| 5,370,121 A | 12/1994 | Reichenberger |
| 5,371,483 A | 12/1994 | Bhardwaj |
| 5,380,280 A | 1/1995 | Peterson |
| 5,391,140 A | 2/1995 | Schaetzle et al. |
| 5,419,327 A | 5/1995 | Rohwedder |
| 5,435,311 A | 7/1995 | Umemura |
| 5,458,596 A | 10/1995 | Lax |
| 5,460,595 A | 10/1995 | Hall et al. |
| 5,471,988 A | 12/1995 | Fujio |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenschein |
| 5,524,624 A | 6/1996 | Tepper |
| 5,526,812 A | 6/1996 | Dumoulin et al. |
| 5,526,814 A | 6/1996 | Cline et al. |
| 5,526,815 A | 6/1996 | Granz |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,638,819 A | 6/1997 | Manwaring et al. |
| 5,647,373 A | 7/1997 | Paltieli |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,665,053 A | 9/1997 | Jacobs |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,769,790 A | 6/1998 | Watkins |
| 5,795,297 A | 8/1998 | Daigle |
| 5,795,311 A | 8/1998 | Wess |
| 5,810,888 A | 9/1998 | Fenn |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,871,524 A | 2/1999 | Knowlton |
| 5,873,902 A | 2/1999 | Sanghvi |
| 5,879,303 A | 3/1999 | Averkiou et al. |
| 5,882,557 A | 3/1999 | Hayakawa |
| 5,891,034 A | 4/1999 | Bucholz |
| 5,904,659 A | 5/1999 | Duarte |
| 5,919,219 A | 7/1999 | Knowlton |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,967,980 A | 10/1999 | Ferre et al. |
| 5,968,034 A | 10/1999 | Fulmer |
| 5,971,949 A | 10/1999 | Levin |

| | | | | | | |
|---|---|---|---|---|---|---|
| 5,984,882 | A | 11/1999 | Rosenschein | 6,491,657 B2 | 12/2002 | Rowe |
| 5,997,471 | A | 12/1999 | Gumb et al. | 6,500,121 B1 | 12/2002 | Slayton |
| 5,997,497 | A | 12/1999 | Nita et al. | 6,500,141 B1 | 12/2002 | Irion |
| 6,004,262 | A | 12/1999 | Putz et al. | 6,508,774 B1 | 1/2003 | Acker et al. |
| 6,007,499 | A | 12/1999 | Martin et al. | 6,511,428 B1 | 1/2003 | Azuma |
| 6,036,646 | A | 3/2000 | Barthe | 6,514,244 B2 | 2/2003 | Pope |
| 6,039,048 | A | 3/2000 | Silberg | 6,524,250 B1 | 2/2003 | Weber |
| 6,042,556 | A | 3/2000 | Beach | 6,540,679 B2 | 4/2003 | Slayton |
| 6,049,159 | A | 4/2000 | Barthe | 6,540,685 B1 | 4/2003 | Rhoads et al. |
| 6,050,943 | A | 4/2000 | Slayton | 6,554,771 B1 | 4/2003 | Buil et al. |
| 6,059,727 | A | 5/2000 | Fowlkes | 6,569,099 B1 | 5/2003 | Babaev |
| 6,071,239 | A | 6/2000 | Cribbs | 6,595,934 B1 | 7/2003 | Hissong |
| 6,080,108 | A | 6/2000 | Dunham | 6,599,256 B1 | 7/2003 | Acker |
| 6,086,535 | A | 7/2000 | Ishibashi | 6,607,498 B2 | 8/2003 | Eshel |
| 6,086,580 | A | 7/2000 | Mordon et al. | 6,623,430 B1 | 9/2003 | Slayton |
| 6,090,054 | A | 7/2000 | Tagishi | 6,626,854 B2 | 9/2003 | Friedman |
| 6,093,883 | A | 7/2000 | Sanghvi | 6,626,855 B1 | 9/2003 | Weng |
| 6,106,469 | A | 8/2000 | Suzuki et al. | 6,645,162 B2 | 11/2003 | Friedman |
| 6,113,558 | A | 9/2000 | Rosenschein | 6,662,054 B2 | 12/2003 | Kreindel et al. |
| 6,113,559 | A | 9/2000 | Klopotek | 6,663,627 B2 | 12/2003 | Francischelli |
| 6,120,452 | A | 9/2000 | Barthe | 6,665,806 B1 | 12/2003 | Shimizu |
| 6,135,971 | A | 10/2000 | Hutchinson et al. | 6,666,835 B2 | 12/2003 | Martin |
| 6,139,499 | A | 10/2000 | Wilk | 6,685,640 B1 | 2/2004 | Fry |
| 6,159,150 | A | 12/2000 | Yale et al. | 6,692,450 B1 | 2/2004 | Coleman |
| 6,171,244 | B1 | 1/2001 | Finger et al. | 6,699,237 B2 | 3/2004 | Weber |
| 6,176,840 | B1 | 1/2001 | Nishimura | 6,719,449 B1 | 4/2004 | Laugharn |
| 6,183,426 | B1 | 2/2001 | Akisada | 6,719,694 B2 | 4/2004 | Weng |
| 6,183,502 | B1 | 2/2001 | Takeuchi | 6,749,624 B2 | 6/2004 | Knowlton |
| 6,183,773 | B1 | 2/2001 | Anderson | 6,775,404 B1 | 8/2004 | Pagoulatos et al. |
| 6,190,323 | B1 | 2/2001 | Digs | 6,824,516 B2 | 11/2004 | Batten et al. |
| 6,190,336 | B1 | 2/2001 | Duarte | 6,835,940 B2 | 12/2004 | Morikawa et al. |
| 6,213,948 | B1 | 4/2001 | Barthe | 6,875,176 B2 | 4/2005 | Mourad et al. |
| 6,216,029 | B1 | 4/2001 | Paltieli | 6,887,239 B2 | 5/2005 | Elstrom |
| 6,233,476 | B1 | 5/2001 | Strommer et al. | 6,905,466 B2 | 6/2005 | Salgo |
| 6,234,990 | B1 | 5/2001 | Rowe et al. | 6,920,883 B2 | 7/2005 | Bessette |
| 6,241,753 | B1 | 6/2001 | Knowlton | 6,921,371 B2 | 7/2005 | Wilson |
| 6,246,898 | B1 | 6/2001 | Vesely et al. | 6,932,771 B2 | 8/2005 | Whitmore |
| 6,251,088 | B1 | 6/2001 | Kaufman et al. | 6,936,044 B2 | 8/2005 | McDaniel |
| 6,268,405 | B1 | 7/2001 | Yao | 6,936,046 B2 | 8/2005 | Hissong |
| 6,273,864 | B1 | 8/2001 | Duarte | 6,948,843 B2 | 9/2005 | Laugharn et al. |
| 6,296,619 | B1 | 10/2001 | Brisken | 6,953,941 B2 | 10/2005 | Nakano et al. |
| 6,301,989 | B1 | 10/2001 | Brown et al. | 6,958,043 B2 | 10/2005 | Hissong |
| 6,311,090 | B1 | 10/2001 | Knowlton | 6,974,417 B2 | 12/2005 | Lockwood |
| 6,315,741 | B1 | 11/2001 | Martin | 6,976,492 B2 | 12/2005 | Ingle |
| 6,322,509 | B1 | 11/2001 | Pan et al. | 6,992,305 B2 | 1/2006 | Maezawa et al. |
| 6,322,532 | B1 | 11/2001 | D'Sa | 6,997,923 B2 | 2/2006 | Anderson |
| 6,325,540 | B1 | 12/2001 | Lounsberry et al. | 7,006,874 B2 | 2/2006 | Knowlton |
| 6,325,769 | B1 * | 12/2001 | Klopotek ........................... 601/2 | 7,020,528 B2 | 3/2006 | Neev |
| 6,325,798 | B1 | 12/2001 | Edwards et al. | 7,022,089 B2 | 4/2006 | Ooba |
| 6,350,276 | B1 | 2/2002 | Knowlton | 7,058,440 B2 | 6/2006 | Heuscher et al. |
| 6,361,531 | B1 | 3/2002 | Hissong | 7,063,666 B2 | 6/2006 | Weng |
| 6,375,672 | B1 | 4/2002 | Aksan | 7,070,565 B2 | 7/2006 | Vaezy et al. |
| 6,377,854 | B1 | 4/2002 | Knowlton | 7,074,218 B2 | 7/2006 | Washington et al. |
| 6,377,855 | B1 | 4/2002 | Knowlton | 7,094,252 B2 | 8/2006 | Koop |
| 6,381,497 | B1 | 4/2002 | Knowlton | 7,115,123 B2 | 10/2006 | Knowlton |
| 6,381,498 | B1 | 4/2002 | Knowlton | 7,142,905 B2 | 11/2006 | Slayton |
| 6,387,380 | B1 | 5/2002 | Knowlton | 7,179,238 B2 | 2/2007 | Hissong |
| 6,390,982 | B1 | 5/2002 | Bova et al. | 7,189,230 B2 | 3/2007 | Knowlton |
| 6,405,090 | B1 | 6/2002 | Knowlton | 7,229,411 B2 | 6/2007 | Slayton |
| 6,409,720 | B1 | 6/2002 | Hissong | 7,235,592 B2 | 6/2007 | Muratoglu |
| 6,413,253 | B1 | 7/2002 | Koop | 7,258,674 B2 | 8/2007 | Cribbs |
| 6,413,254 | B1 | 7/2002 | Hissong | 7,273,459 B2 | 9/2007 | Desilets |
| 6,419,648 | B1 | 7/2002 | Vitek | 7,297,117 B2 | 11/2007 | Trucco et al. |
| 6,425,865 | B1 | 7/2002 | Salcudean | 7,347,855 B2 | 3/2008 | Eshel |
| 6,425,867 | B1 | 7/2002 | Vaezy | RE40,403 E | 6/2008 | Cho et al. |
| 6,425,912 | B1 | 7/2002 | Knowlton | 7,393,325 B2 | 7/2008 | Barthe |
| 6,428,477 | B1 | 8/2002 | Mason | 7,491,171 B2 | 2/2009 | Barthe et al. |
| 6,428,532 | B1 | 8/2002 | Doukas | 7,601,120 B2 | 10/2009 | Moilanen et al. |
| 6,430,446 | B1 | 8/2002 | Knowlton | 7,615,015 B2 | 11/2009 | Coleman |
| 6,432,067 | B1 | 8/2002 | Martin | 7,824,348 B2 | 11/2010 | Barthe et al. |
| 6,432,101 | B1 | 8/2002 | Weber | 8,057,389 B2 | 11/2011 | Barthe et al. |
| 6,436,061 | B1 | 8/2002 | Costantino | 8,128,618 B2 | 3/2012 | Gliklich et al. |
| 6,438,424 | B1 | 8/2002 | Knowlton | 2001/0009997 A1 | 7/2001 | Pope |
| 6,440,071 | B1 | 8/2002 | Slayton | 2001/0014780 A1 | 8/2001 | Martin et al. |
| 6,440,121 | B1 | 8/2002 | Weber | 2001/0039380 A1 | 11/2001 | Larson et al. |
| 6,443,914 | B1 | 9/2002 | Costantino | 2001/0041880 A1 | 11/2001 | Brisken |
| 6,453,202 | B1 | 9/2002 | Knowlton | 2002/0000763 A1 | 1/2002 | Jones |
| 6,461,378 | B1 | 10/2002 | Knowlton | 2002/0040199 A1 | 4/2002 | Klopotek |
| 6,470,216 | B1 | 10/2002 | Knowlton | 2002/0040442 A1 | 4/2002 | Ishidera |

| | | |
|---|---|---|
| 2002/0055702 A1 | 5/2002 | Atala |
| 2002/0062077 A1 | 5/2002 | Emmenegger et al. |
| 2002/0062142 A1* | 5/2002 | Knowlton ................ 607/99 |
| 2002/0082528 A1 | 6/2002 | Friedman |
| 2002/0082589 A1 | 6/2002 | Friedman |
| 2002/0095143 A1 | 7/2002 | Key |
| 2002/0128648 A1 | 9/2002 | Weber |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193831 A1 | 12/2002 | Smith |
| 2003/0014039 A1 | 1/2003 | Barzell et al. |
| 2003/0018255 A1 | 1/2003 | Martin |
| 2003/0028113 A1 | 2/2003 | Gilbert et al. |
| 2003/0032900 A1 | 2/2003 | Ella |
| 2003/0036706 A1 | 2/2003 | Slayton |
| 2003/0040739 A1 | 2/2003 | Koop |
| 2003/0050678 A1 | 3/2003 | Sierra |
| 2003/0060736 A1 | 3/2003 | Martin et al. |
| 2003/0065313 A1 | 4/2003 | Koop |
| 2003/0074023 A1 | 4/2003 | Kaplan |
| 2003/0083536 A1 | 5/2003 | Eshel |
| 2003/0097071 A1 | 5/2003 | Halmann et al. |
| 2003/0125629 A1 | 7/2003 | Ustuner |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0059266 A1 | 3/2004 | Fry |
| 2004/0073079 A1 | 4/2004 | Altshuler et al. |
| 2004/0073113 A1 | 4/2004 | Salgo |
| 2004/0073116 A1 | 4/2004 | Smith |
| 2004/0082859 A1 | 4/2004 | Schaer |
| 2004/0102697 A1 | 5/2004 | Evron |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0267252 A1 | 12/2004 | Washington |
| 2005/0033201 A1 | 2/2005 | Takahashi |
| 2005/0055073 A1 | 3/2005 | Weber |
| 2005/0070961 A1 | 3/2005 | Maki et al. |
| 2005/0074407 A1 | 4/2005 | Smith |
| 2005/0080469 A1 | 4/2005 | Larson |
| 2005/0113689 A1 | 5/2005 | Gritzky |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0228281 A1 | 10/2005 | Nefos |
| 2005/0256406 A1 | 11/2005 | Barthe |
| 2005/0261584 A1 | 11/2005 | Eshel |
| 2005/0267454 A1 | 12/2005 | Hissong |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0111744 A1 | 5/2006 | Makin |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0206105 A1 | 9/2006 | Chopra |
| 2006/0241440 A1 | 10/2006 | Eshel |
| 2006/0241442 A1 | 10/2006 | Barthe |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gliklich |
| 2007/0035201 A1 | 2/2007 | Desilets |
| 2007/0055154 A1 | 3/2007 | Torbati |
| 2007/0055156 A1 | 3/2007 | Desilets |
| 2007/0087060 A1 | 4/2007 | Dietrich |
| 2007/0088346 A1 | 4/2007 | Mirizzi et al. |
| 2007/0167709 A1 | 7/2007 | Slayton |
| 2007/0208253 A1 | 9/2007 | Slayton |
| 2008/0071255 A1 | 3/2008 | Barthe |
| 2008/0086054 A1 | 4/2008 | Slayton |
| 2008/0200813 A1 | 8/2008 | Quistgaard |
| 2008/0214966 A1 | 9/2008 | Slayton |
| 2008/0221491 A1 | 9/2008 | Slayton |
| 2008/0275342 A1 | 11/2008 | Barthe |
| 2008/0281237 A1 | 11/2008 | Slayton |
| 2008/0281255 A1 | 11/2008 | Slayton |
| 2008/0294073 A1 | 11/2008 | Barthe |
| 2009/0069677 A1 | 3/2009 | Chen et al. |
| 2009/0318909 A1 | 12/2009 | Debenedictis et al. |

FOREIGN PATENT DOCUMENTS

| | | |
|---|---|---|
| DE | 10140064 A1 | 3/2003 |
| DE | 10219217 | 11/2003 |
| DE | 10219297 | 11/2003 |
| DE | 20314479 | 3/2004 |
| EP | 0344773 A2 | 12/1989 |
| EP | 1479412 A1 | 11/1991 |
| EP | 0473553 | 4/1992 |
| EP | 0661029 A1 | 7/1995 |
| EP | 1050322 A1 | 11/2000 |
| EP | 1234566 | 8/2002 |
| EP | 1262160 | 12/2002 |
| GB | 2113099 | 8/1983 |
| JP | 3123559 | 5/1991 |
| JP | 03136642 | 6/1991 |
| JP | 4089058 | 3/1992 |
| JP | 7080087 | 3/1995 |
| JP | 7222782 | 8/1995 |
| JP | 11-505440 | 5/1999 |
| JP | 2002078764 | 3/2002 |
| JP | 2002-537939 | 11/2002 |
| JP | 2003050298 | 2/2003 |
| JP | 2004-147719 | 5/2004 |
| JP | 2005323213 | 11/2005 |
| KR | 1020010024871 | 3/2001 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |

| | | |
|---|---|---|
| KR | 1020070114105 | 11/2007 |
| WO | WO 96/25888 | 8/1996 |
| WO | WO 9735518 | 10/1997 |
| WO | WO 9832379 | 7/1998 |
| WO | WO 9933520 | 7/1999 |
| WO | WO 9949788 | 10/1999 |
| WO | WO 0015300 | 3/2000 |
| WO | WO 0021612 | 4/2000 |
| WO | WO 0053113 | 9/2000 |
| WO | WO 0128623 | 4/2001 |
| WO | WO 0182777 | 11/2001 |
| WO | WO 0182778 | 11/2001 |
| WO | WO 0187161 | 11/2001 |
| WO | WO 0209813 | 2/2002 |
| WO | WO 0224050 | 3/2002 |
| WO | WO 0292168 | 11/2002 |
| WO | WO 03065347 | 8/2003 |
| WO | WO 03070105 | 8/2003 |
| WO | WO 03077833 | 9/2003 |
| WO | WO 03086215 | 10/2003 |
| WO | WO 03/096883 A2 | 11/2003 |
| WO | WO 03099177 | 12/2003 |
| WO | WO 03101530 | 12/2003 |
| WO | WO 2005090978 | 9/2005 |
| WO | WO 2006036870 | 4/2006 |
| WO | WO 2006042168 | 4/2006 |
| WO | WO 2006042201 | 4/2006 |
| WO | WO2009013729 | 1/2009 |

OTHER PUBLICATIONS

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Chen, L. et al., "Effect of Blood Perfusion on the ablation of liver perenchyma with high intensity focused ultrasound," Phys. Med. Biol; 38:1661-1673; 1993b.

Coon, Joshua et al., "Protein identification using sequential ion/ion reactions and tandem mass spectometry" Proceedings of the National Academy of Sciences of the USA, vol. 102, No. 27, Jul. 27, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444, 456.

Damianou et al., "Application of the Thermal Dose Concept for Predicting the Necrosed Tissue Volume During Ultrasound Surgery," 1993 IEEE Ultrasound Symposium, pp. 1199-1202.

Daum et al., Design and Evaluation of a Feedback Based Phased Array System for Ultrasound Surgery, IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Fry, W.J. et al., "Production of Focal Destructive Lesions in the Central Nervous System with Ultrasound," J. Neurosurg., 11:471-478; 1954.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.

Harr, G.R. et al., "Tissue Destruction with Focused Ultrasound in Vivo," Eur. Urol. 23 (suppl. 1):8-11; 1993.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jeffers et al., "Evaluation of the Effect of Cavitation Activity on Drug-Ultrasound Synergisms," 1993 IEEE Ultrasonics Symposium, pp. 925-928.

Jenne, J., et al., "Temperature Mapping for High Energy US-Therapy", 1994 Ultrasonics Symposium, pp. 1879-1882.

Johnson, S.A., et al., "Non-lnstrusive Measurement of Microwave and Ultrasound-Induced Hyperthermia by Acoustic Temperature Tornography", Ultrasonics Symposium Proceedings, pp. 977-982.

Madersbacher, S. et al., "Tissue Ablation in Bening Prostatic Hyperplasia with High Intensity Focused Ultrasound," Dur. Urol., 23 (suppl. 1):39-43; 1993.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Confirmed Bulk Ablation and Therapy Monitoring Using Intracorporeal Image-Treat Ultrasound Arrays," 4th International Symposium on Theraputic Ultrasound, Sep. 19, 2004.

Makin et al., "Miniaturized Ultrasound Arrays for Interstitial Ablation and Imaging," UltraSound Med. Biol. 2005, Nov. 1, 2005, pp. 1539-1550, vol. 31(11).

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Mitragotri, S., "Healing sound: the use of ultrasound in drug delivery and other therapeutic applications," Nature Reviews; Drug Delivery, pp. 255-260, vol. 4.

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Saad et al., "Ultrasound-Enhanced Effects of Adriamycin Against Murine Tumors," Ultrasound in Med. & Biol. vol. 18, No. 8, pp. 715-723 (1992).

Sanghvi, N. T., et al., "Transrectal Ablation of Prostate Tissue Using Focused Ultrasound," 1993 Ultrasonics Symposium, IEEE, pp. 1207-1210.

Sassen, Sander, "ATI's R520 architecture, the new king of the hill?" http://www.hardwareanalysis.com/content/article/1813, Sep. 16, 2005, 2 pages.

Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Simon et al., "Applications of Lipid-Coated Microbubble Ultrasonic Contrast to Tumor Therapy," Ultrasound in Med. & Biol. vol. 19, No. 2, pp. 123-125 (1993).

Smith, Nadine Barrie, et al., "Non-invasive in Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Ueno, S., et al., "Ultrasound Termometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.

White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1.

Arthur et al., "Non-invasive estimation of hyperthermia temperatures with ultrasound," Int. J. Hyperthermia, Sep. 2005, 21(6), pp. 589-600.

* cited by examiner

METHODS FOR TREATMENT OF SWEAT GLANDS

CROSS-REFERENCE TO RELATED APPLICATIONS

This application is a continuation of U.S. application Ser. No. 11/163,152 titled "METHOD AND SYSTEM FOR TREATMENT OF SWEAT GLANDS" filed on Oct. 6, 2005, now abandoned, which claims the benefit of priority to U.S. Provisional Application No. 60/616,752, titled "METHOD AND SYSTEM FOR TREATMENT OF SWEAT GLANDS" filed on Oct. 6, 2004.

BACKGROUND

1. Field of the Invention

This invention generally relates to a therapeutic ultrasound method and system, and more particularly, to a method and system for ultrasound treatment for superficial tissue containing sweat glands.

2. Description of the Related Art

The sweat glands in the body are of divided into apocrine and eccrine glands. Apocrine glands are similar to sebaceous glands, and are present mainly in the axillae. These glands, like sebaceous glands, secrete an oily proteinaceous product into the follicles. Bacterial digestion of apocrine sweat is largely responsible for underarm "body odor". Similarly, eccrine sweat glands are present deep in the dermis in the palms, soles and armpits and are responsible for temperature regulation resulting from sweating. Excessive activity of these glands also results in copious amounts of abnormal sweating ("hyperhidrosis"), primarily under autonomic neuronal control. Reduction of sweating from under the armpits and other regions is a particularly desirable effect within the modern society. Presently, chemical antiperspirants and deodorants are used frequently as a matter of personal hygiene. Antiperspirants are aluminum based salts that block the sweat gland ducts. The deodorant changes the pH of the skin milieu thereby minimizing the presence of (smell inducing) bacteria. The effects with both these components however, are temporary and these chemicals are known to irritate the skin in a good percentage of users.

Further, there is currently a significant unmet need in managing the excessive sweating and concomitant issues with odor as a result of Hydradenitis suppurativa (irritable infected armpit). This acne-like process in apocine follicles also causes hydradenitis suppurativa, which is often a devastating condition in which very painful cysts and scarring occurs repeatedly in the axillae. The etiology (causes) of this clinical condition is not well understood. However, there are a number of marginally effective approaches to manage this condition. Retinoid drug therapy works marginally but is associated with severe toxicity. Some prescription formulations of antiperspirants can be used, but they are not particularly effective. These preparations can be applied with the addition of an iontophoretic device. This technique however, is not known to be any more effective than the formulation. The sweat glands can be surgically removed from the armpits and/or the sympathetic nerve supply can be interrupted surgically. This approach is fraught with its own drawbacks in terms of morbidity, scarring and cost. BOTOX® is being used ever more for paralyzing the nerve connections that induce excessive sweating in the armpits. However, this is a new approach yet to be completely validated. This technique requires multiple injections (painful) and the results last a few months only (3-4 months), hence need to be repeated. This technique does not get rid of the odor associated with the condition.

SUMMARY OF THE INVENTION

The present invention describes a non-invasive method and system for using therapeutic ultrasound energy for the treatment of conditions resulting from sweat gland disorders. An ultrasound system and method comprises a transducer probe and control system configured to deliver ultrasound energy to the regions of the superficial tissue (e.g., skin) such that the energy can be deposited at the particular depth at which the aberrant sweat gland population is located below the skin surface.

In accordance with various exemplary embodiments, the ultrasound transducer can be driven at a number of different frequency regimes such that the depth and shape of energy concentration can match the region of treatment. In addition, the ultrasound source or beam radiated from the transducer can be highly focused, weakly focused, or divergent, each in a cylindrical or spherical geometric configuration, and/or can also be planar to radiate a directive beam through the tissue, or various other configurations. Further, the ultrasound field can be varied spatially and temporally in a suitable manner to achieve the optimal tissue effect and/or type of conformal lesion for treating the sweat glands.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various components and processing steps. It should be appreciated that such components and steps may be realized by any number of hardware components configured to perform the specified functions. For example, the present invention may be configured with various medical treatment devices, visual imaging and display devices, input terminals and the like, which may carry out a variety of functions under the control of one or more control systems or other control devices. In addition, the present invention may be practiced in any number of medical or treatment contexts and that the exemplary embodiments relating to a method and system for sweat gland treatment as described herein are merely a few of the exemplary applications for the invention. For example, the principles, features and methods discussed may be applied to any medical or other tissue or treatment application.

In accordance with various aspects of the present invention, a non-invasive method and system for the treatment of sweat glands is described. In accordance with an exemplary embodiment, an ultrasound transducer probe and control system are configured to deliver ultrasound energy to a targeted/specified depth and zone where the sweat gland population is required to be treated. The ultrasound beam from the transducer probe can be spatially and/or temporally adjusted, modified or otherwise controlled to match the adequate treatment of the sweat glands in the region of interest.

Figure 1:
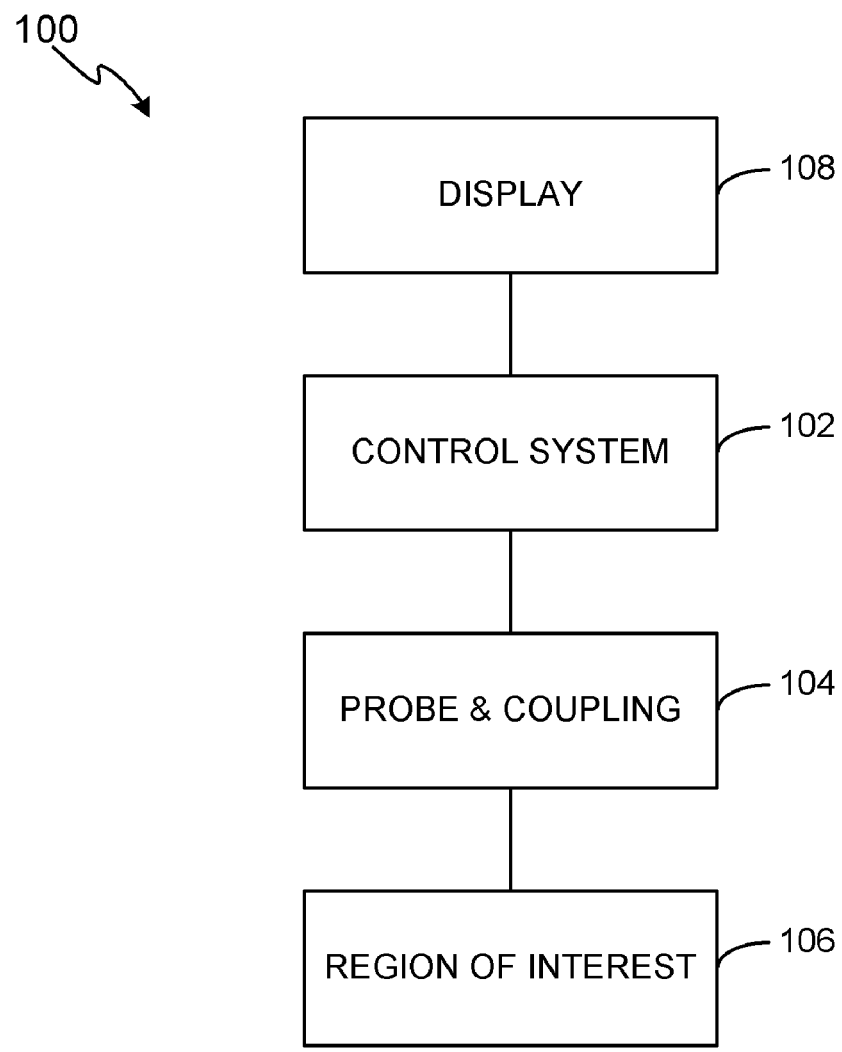
FIG. 1 illustrates a block diagram of an ultrasound therapy system for treating sweat glands in accordance with an exemplary embodiment of the present invention.

For example, in accordance with an exemplary embodiment, with reference to FIG. 1, an exemplary treatment system 100 configured to treat a region of interest (ROI) 106 comprises a control system 102, an imaging/therapy probe with acoustic coupling 104, and a display system 108.

Control system 102 and display 108 can comprise various configurations for controlling functionality of probe 104 and system 100, including for example a microprocessor with software and a plurality of input/output and communication devices, a system for controlling electronic and/or mechanical scanning and/or multiplexing of transducers, a system for power delivery, systems for monitoring, systems for sensing the spatial parameters and/or temporal parameters of the probe and transducers, and/or systems for handling user input and recording treatment input and results, among others. Imaging/therapy probe 104 can comprise various probe and/or transducer configurations. For example, probe 104 can be configured for a combined dual-mode imaging/therapy transducer, coupled or co-housed imaging/therapy transducers, a separate therapy probe and separate imaging probe, or a single therapy probe. In accordance with exemplary embodiments, imaging transducers may operate at frequencies from approximately 2 MHz to 75 MHz or more, while therapy energy can be delivered at frequencies from approximately 500 kHz to 15 MHz, with 2 MHz to 25 MHz being typical.

Figure 2A:
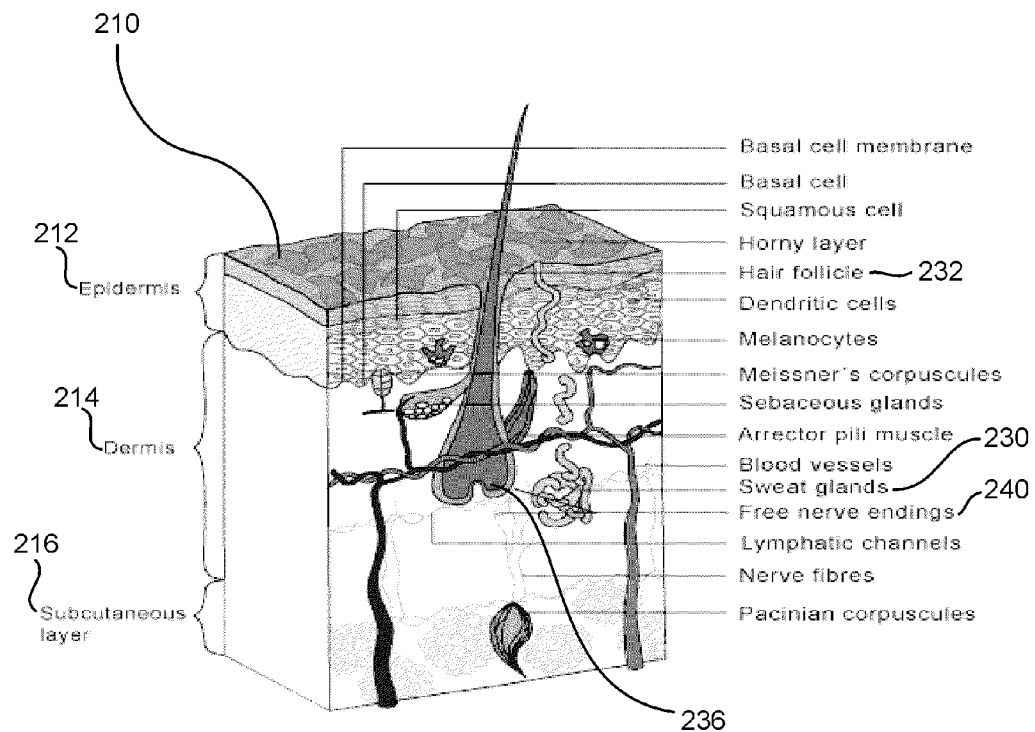
FIGS. 2A and 2B illustrate schematic diagrams of ultrasound treatment systems configured to treat the sweat glands via direct targeting of heating and damage within the treatment layer in accordance with various exemplary embodiments of the present invention.

With reference to FIG. 2A, sweat glands 230 are generally located within a dermis layer 214 at a depth close to hair bulbs 236. In order to treat sweat glands that require treatment in particular anatomical sites, such as, for example but not limited to, the axillary region (armpit), the palms and soles, an ultrasound transducer probe can be coupled to the skin tissue using one of the numerous coupling media, such as water, mineral oils, gels, and the like.

Figure 2B:
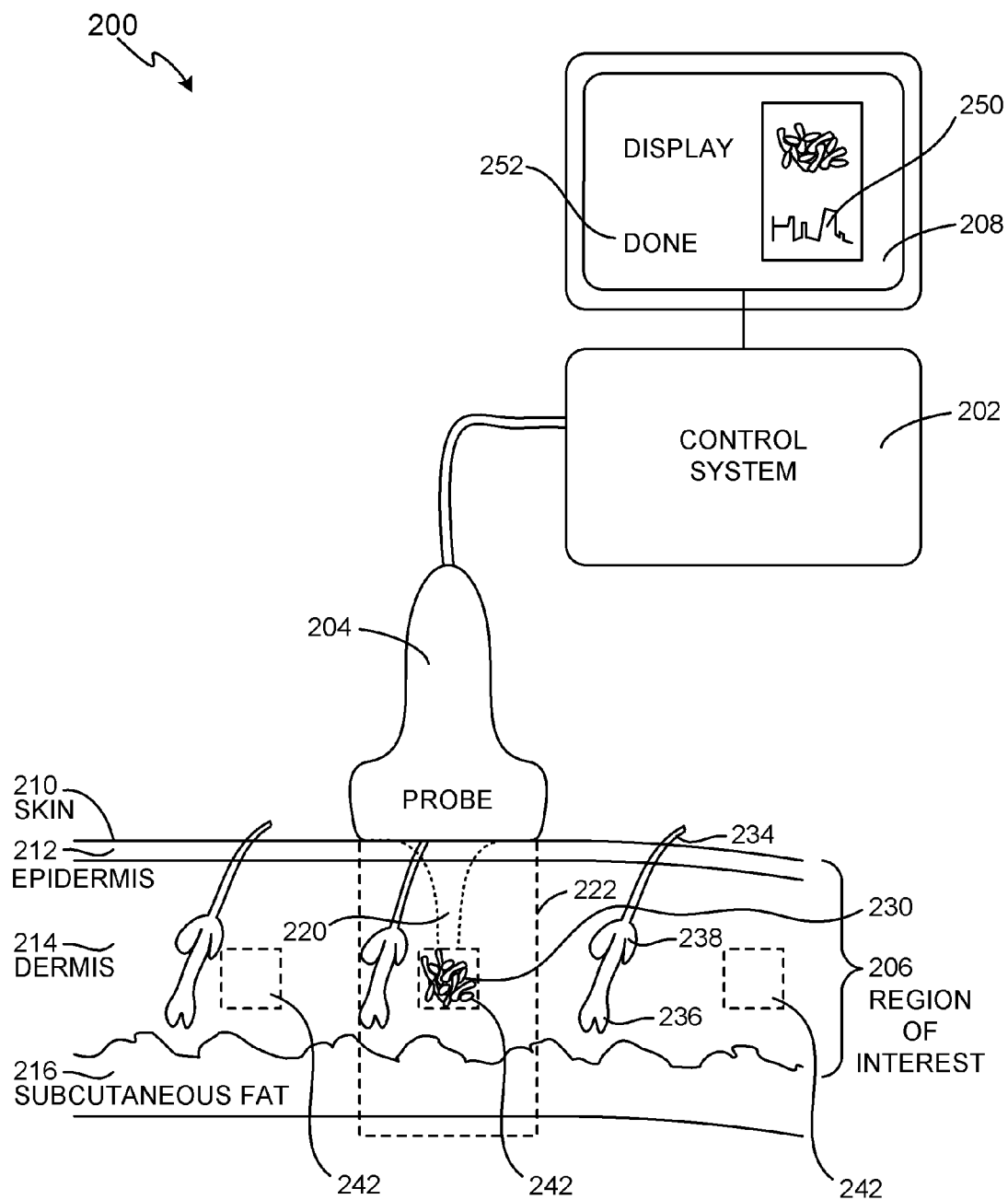

For example, with reference to FIG. 2B, in accordance with an exemplary embodiment an exemplary treatment method and system are configured for initially imaging a region 222 within a region of interest 206 and displaying that region 224 on a display 208 to facilitate localization of the treatment area and surrounding structures, e.g., identification of sweat glands 230, such as within the axillary region (armpit), the palms and soles or any other tissue or skin surrounding sweat glands. After localization, delivery of ultrasound energy 220 at a depth, distribution, timing, and energy level to achieve the desired therapeutic effect of thermal ablation to treat a sweat gland 230 is provided. Before, during, and/or after therapy, i.e., before, during and/or after delivery of ultrasound energy, monitoring of the treatment area and surrounding structures can be conducted to further planning and assessing of the results and/or providing feedback to control system 202 and a system operator.

In accordance with an exemplary embodiment, localization can be facilitated through ultrasound imaging that can be used to define the position of a sweat gland 230 and/or the depth of sweat glands 230 over a region of interest before depositing in a defined pattern at a target region 220. Such glands can be seen lying along hair follicles 232 and bulbs 236 and their image may be further enhanced via signal and image processing. Ultrasound imaging can also be used for safety purposes, namely, to avoid injuring vital structures, such as nerve endings 240. In accordance with other exemplary embodiments, localization can also be accomplished without imaging region 222, but instead can be based on prior known depths of sweat glands or other target regions, and thus be configured geometrically and/or electronically to selectively deposit energy at a particular known depth below skin surface 210 to a target region 220.

The ultrasound beam from probe 204 can be spatially and/or temporally controlled by changing the spatial parameters of the transducer, such as the placement, distance, treatment depth and transducer structure, as well as by changing the temporal parameters of transducer, such as the frequency, drive amplitude, and timing, with such control handled via control system 202. For example, in some applications, the temporal energy exposure at one location may range from approximately to 40 ms to 40 seconds, while the corresponding source frequency can suitably range from approximately 500 kHz to 15 MHz. Such spatial and temporal parameters can also be suitably monitored and/or utilized in open-loop and/or closed-loop feedback systems within treatment system 200. As a result of such spatial and/or temporal control, conformal lesions of various, specifically targeted, shapes, sizes and orientations can be configured within target region 220.

In accordance with an exemplary embodiment, the treatment resulting from ultrasound energy delivery in the region of sweat glands 230 can be used to achieve selective ablation of regions of sub-epidermal region (0.5-10 mm diameter zones). For example, one or more treated zones 242 can be configured to produce regions of ablative damage in spatially defined patterns, such as a discrete locus of spaced treatment spots or two- or three-dimensional matrix of damage or destroyed tissue, e.g., a matrix of cross-stitched, ellipsoidal/cigar-shaped, wedge-shaped, mushroom-shaped or any other conformal lesions, rather than heating and destroying the entire volume of the target layer of tissue. In such a treatment where surrounding regions are spared of damage, the surrounding undamaged tissue aids rapid healing and recovery.

In accordance with another exemplary embodiment, a whole contiguous sheet of treatment area can be achieved, whereby all the sweat glands within the said area are ablated. In addition to selective treatment of sweat gland regions, in accordance with another exemplary embodiment, treatment system 200 could be configured to "carpet bomb" the fat layer at 1-7 mm depth, e.g., up to 90% of the sweat glands in the armpit can be ablated without any physiologic issues.

In accordance with another exemplary embodiment of the present invention, an exemplary monitoring method may comprise monitoring the temperature profile or other tissue parameters of the region of interest 206, such as attenuation, speed of sound, or mechanical properties such as stiffness and strain of the treatment region and suitably adjust the spatial and/or temporal characteristics and energy levels of the ultrasound therapy transducer of probe 204. The results of such monitoring techniques may be indicated on display 208 by means of one-, two-, or three-dimensional images of monitoring results 250, or may simply comprise a success or fail-type indicator 252, or combinations thereof. Additional treatment monitoring techniques may be based on one or more of temperature, video, profilometry, and/or stiffness or strain gauges or any other suitable sensing technique.

The non-thermal effects from an acoustic field can also "shock" the sweat producing apocrine and eccrine cells in to reduced activity. These effects mentioned here as examples are, but not limited to, acoustic cavitation, acoustic streaming, inter-cellular shear effects, cell resonant effects, and the like.

In accordance with an exemplary embodiment, focused or directive ultrasound energy can be used for the treatment of sweat glands in the armpit (without the combination of pharmacological formulations). For example, a clinical indication would be to use in the management of Hidradenitis suppurativa. Ultrasound energy deposited at a selective depth can also be used in combination with a number of pharmaceutical formulations that are currently prescribed for the treatment of sweat gland hyperactivity in the axillary region, palms and soles. The ultrasound energy delivered to the target region in combination with the pharmaceutical agents such as BOTOX® or retinoids can help synergistically treat the sweat gland region by, (1) increasing activity of the agents due to the thermal and non-thermal mechanisms, (2) reduced requirement of overall drug dosage, as well as reducing the drug toxicity, (3) increase local effect of drug in a site selective manner.

Figure 3A:
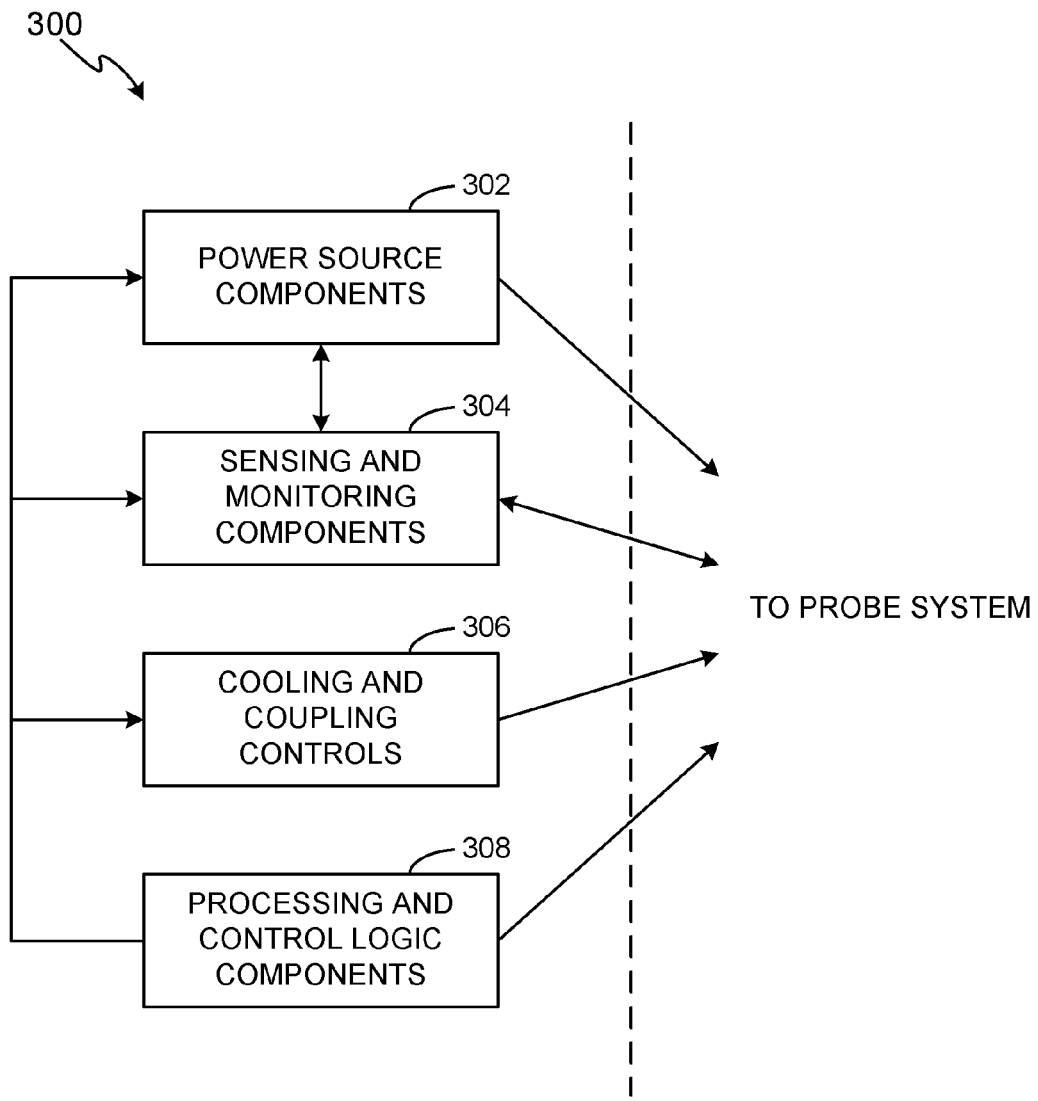
FIGS. 3A and 3B illustrate block diagrams of an exemplary control system in accordance with exemplary embodiments of the present invention.
Figure 3B:
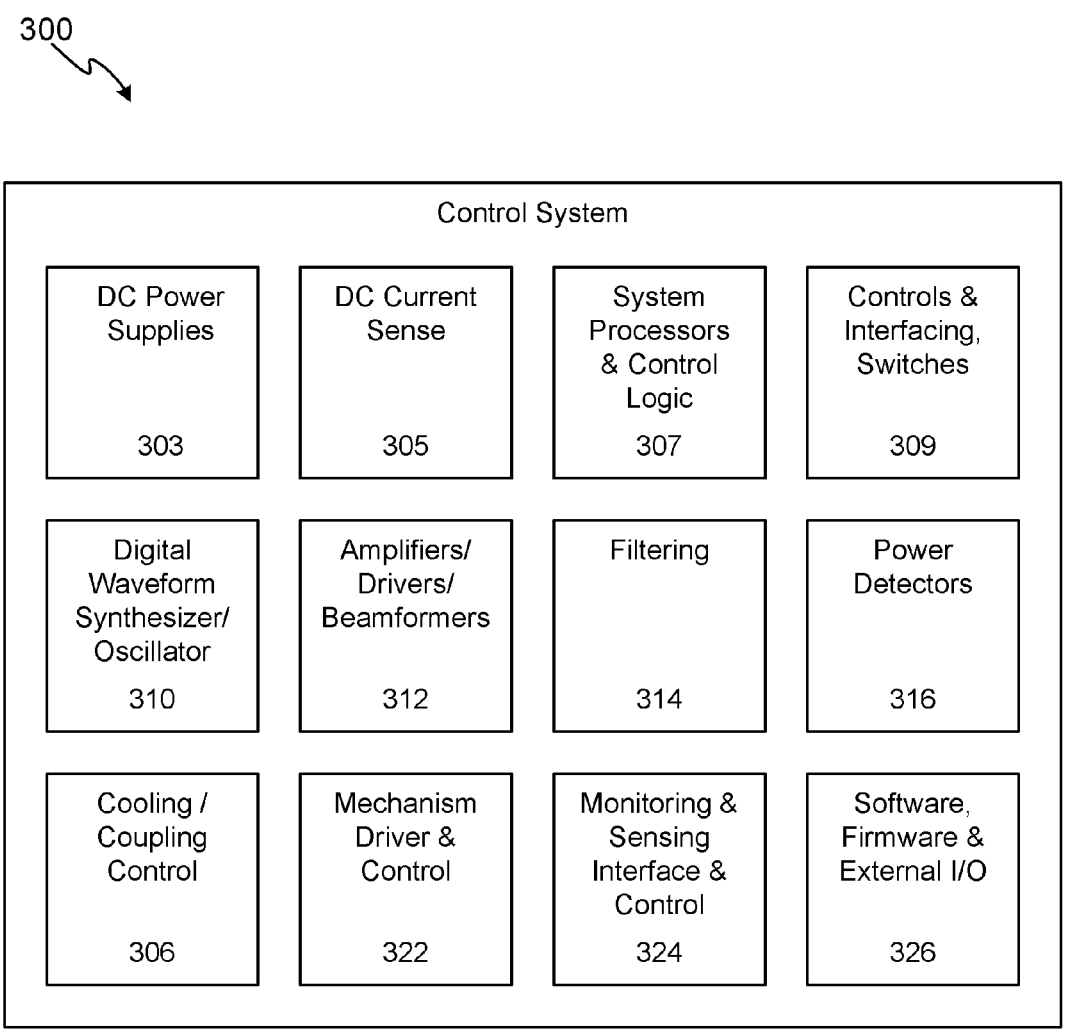

An exemplary control system 202 and display system 208 may be configured in various manners for controlling probe and system functionality for providing the various exemplary treatment methods illustrated above. For example, with reference to FIGS. 3A and 3B, in accordance with exemplary embodiments, an exemplary control system 300 can be configured for coordination and control of the entire therapeutic treatment process to achieve the desired therapeutic effect of thermal ablation to treat a sweat gland. For example, control system 300 can suitably comprise power source components 302, sensing and monitoring components 304, cooling and coupling controls 306, and/or processing and control logic components 308. Control system 300 can be configured and optimized in a variety of ways with more or less subsystems and components to implement the therapeutic system for controlled thermal injury of sweat glands, and the embodiments in FIGS. 3A and 3B are merely for illustration purposes.

For example, for power sourcing components 302, control system 300 can comprise one or more direct current (DC) power supplies 303 configured to provide electrical energy for entire control system 300, including power required by a transducer electronic amplifier/driver 312. A DC current sense device 305 can also be provided to confirm the level of power going into amplifiers/drivers 312 for safety and monitoring purposes.

Amplifiers/drivers 312 can comprise multi-channel or single channel power amplifiers and/or drivers. In accordance with an exemplary embodiment for transducer array configurations, amplifiers/drivers 312 can also be configured with a beamformer to facilitate array focusing. An exemplary beamformer can be electrically excited by an oscillator/digitally controlled waveform synthesizer 310 with related switching logic.

The power sourcing components can also include various filtering configurations 314. For example, switchable harmonic filters and/or matching may be used at the output of amplifier/driver 312 to increase the drive efficiency and effectiveness. Power detection components 316 may also be included to confirm appropriate operation and calibration. For example, electric power and other energy detection components 316 may be used to monitor the amount of power going to an exemplary probe system.

Various sensing and monitoring components 304 may also be suitably implemented within control system 300. For example, in accordance with an exemplary embodiment, monitoring, sensing and interface control components 324 may be configured to operate with various motion detection systems implemented within transducer probe 204 to receive and process information such as acoustic or other spatial and temporal information from a region of interest. Sensing and monitoring components can also include various controls, interfacing and switches 309 and/or power detectors 316. Such sensing and monitoring components 304 can facilitate open-loop and/or closed-loop feedback systems within treatment system 200.

Cooling/coupling control systems 306 may be provided to remove waste heat from an exemplary probe 204, provide a controlled temperature at the superficial tissue interface and deeper into tissue, and/or provide acoustic coupling from transducer probe 204 to region-of-interest 206. Such cooling/coupling control systems 306 can also be configured to operate in both open-loop and/or closed-loop feedback arrangements with various coupling and feedback components.

Processing and control logic components 308 can comprise various system processors and digital control logic 307, such as one or more of microcontrollers, microprocessors, field-programmable gate arrays (FPGAs), computer boards, and associated components, including firmware and control software 326, which interfaces to user controls and interfacing circuits as well as input/output circuits and systems for communications, displays, interfacing, storage, documentation, and other useful functions. System software and firmware 326 controls all initialization, timing, level setting, monitoring, safety monitoring, and all other system functions required to accomplish user-defined treatment objectives. Further, various control switches 308 can also be suitably configured to control operation.

An exemplary transducer probe 204 can also be configured in various manners and comprise a number of reusable and/or disposable components and parts in various embodiments to facilitate its operation. For example, transducer probe 204 can be configured within any type of transducer probe housing or arrangement for facilitating the coupling of transducer to a tissue interface, with such housing comprising various shapes, contours and configurations. Transducer probe 204 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 204 may also comprise cables and connectors; motion mechanisms, motion sensors and encoders; thermal monitoring sensors; and/or user control and status related switches, and indicators such as LEDs. For example, a motion mechanism in probe 204 may be used to controllably create multiple lesions, or sensing of probe motion itself may be used to controllably create multiple lesions and/or stop creation of lesions, e.g. for safety reasons if probe 204 is suddenly jerked or is dropped. In addition, an external motion encoder arm may be used to hold the probe during use, whereby the spatial position and attitude of probe 104 is sent to the control system to help controllably create lesions. Furthermore, other sensing functionality such as profilometers or other imaging modalities may be integrated into the probe in accordance with various exemplary embodiments.

Figure 4A:
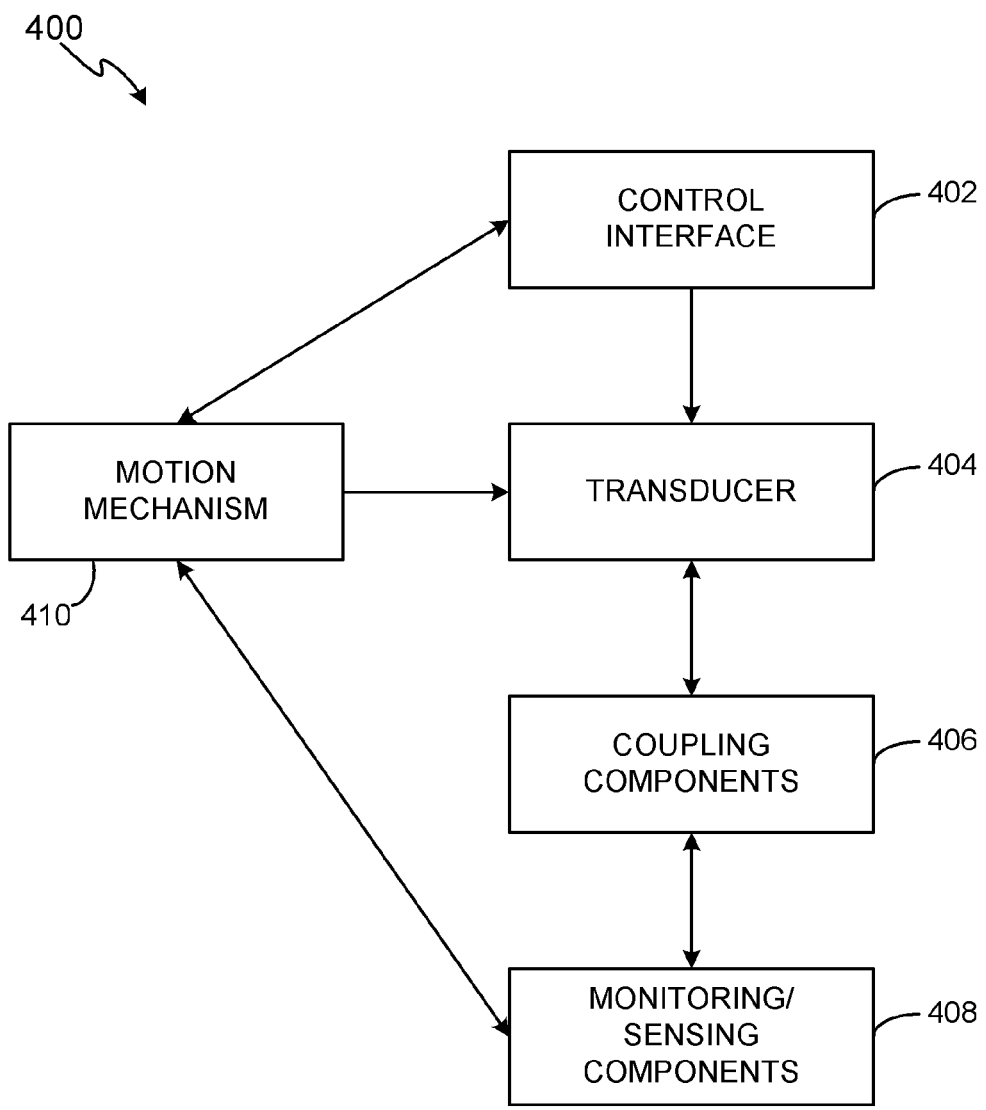
FIGS. 4A and 4B illustrate block diagrams of an exemplary probe system in accordance with exemplary embodiments of the present invention.
Figure 4B:
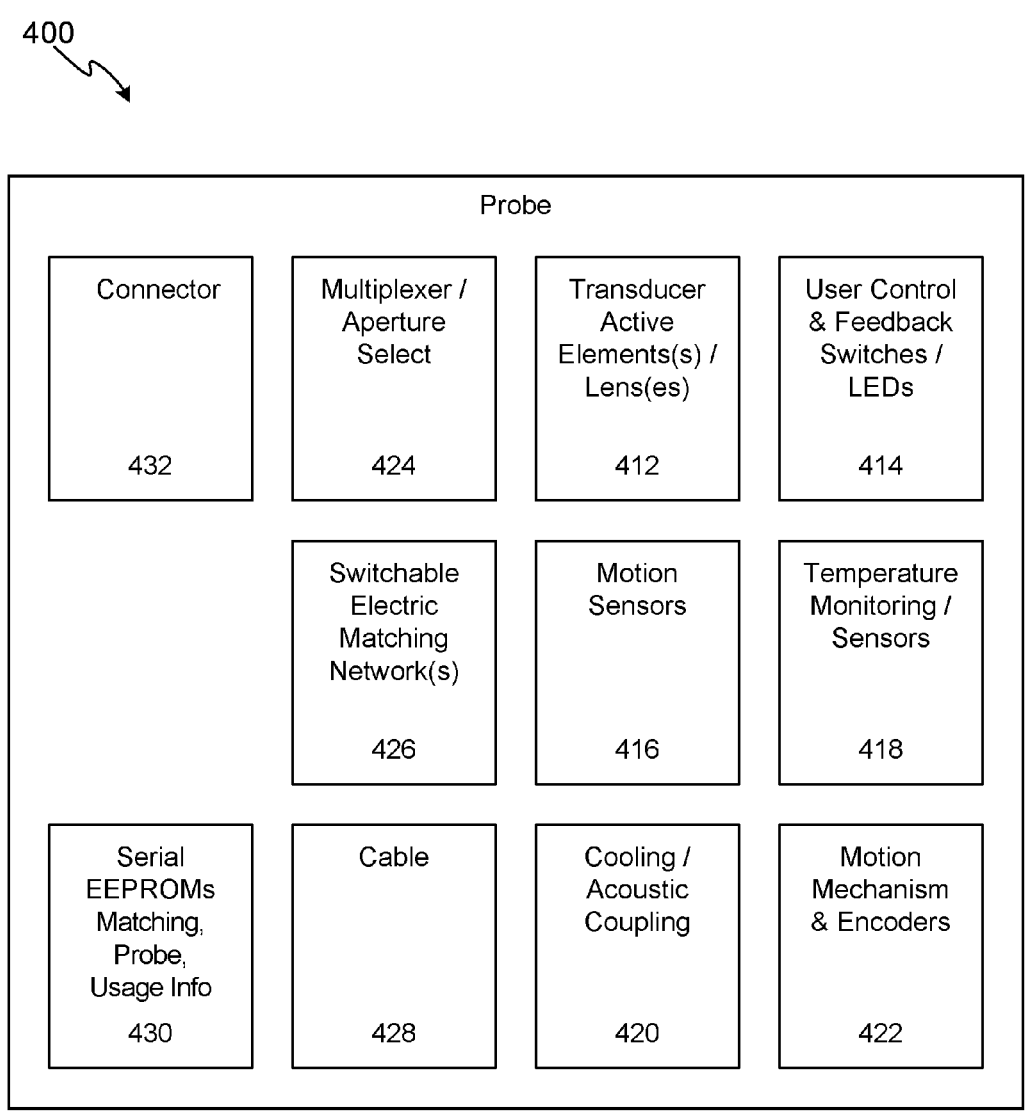

With reference to FIGS. 4A and 4B, in accordance with an exemplary embodiment, a transducer probe 400 can comprise a control interface 402, a transducer 404, coupling components 406, and monitoring/sensing components 408, and/or motion mechanism 410. However, transducer probe 400 can be configured and optimized in a variety of ways with more or less parts and components to provide treatment of sweat glands, and the embodiments in FIGS. 4A and 4B are merely for illustration purposes.

Control interface 402 is configured for interfacing with control system 300 to facilitate control of transducer probe 400. Control interface components 402 can comprise multiplexer/aperture select 424, switchable electric matching networks 426, serial EEPROMs and/or other processing components and matching and probe usage information 430, cable 428 and interface connectors 432.

Coupling components 406 can comprise various devices to facilitate coupling of transducer probe 400 to a region of interest. For example, coupling components 406 can comprise cooling and acoustic coupling system 420 configured for acoustic coupling of ultrasound energy and signals. Acoustic cooling/coupling system 420 with possible connections such as manifolds may be utilized to couple sound into the region-of-interest, control temperature at the interface and deeper into tissue, provide liquid-filled lens focusing, and/or to remove transducer waste heat. Coupling system 420 may facilitate such coupling through use of various coupling mediums, including air and other gases, water and other fluids, gels, solids, and/or any combination thereof, or any other medium that allows for signals to be transmitted between transducer active elements 412 and a region of interest. In addition to providing a coupling function, in accordance with an exemplary embodiment, coupling system 420 can also be configured for providing temperature control during the treatment application. For example, coupling system 420 can be configured for controlled cooling of an interface surface or region between transducer probe 400 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of transducer probe 400.

Figure 11:
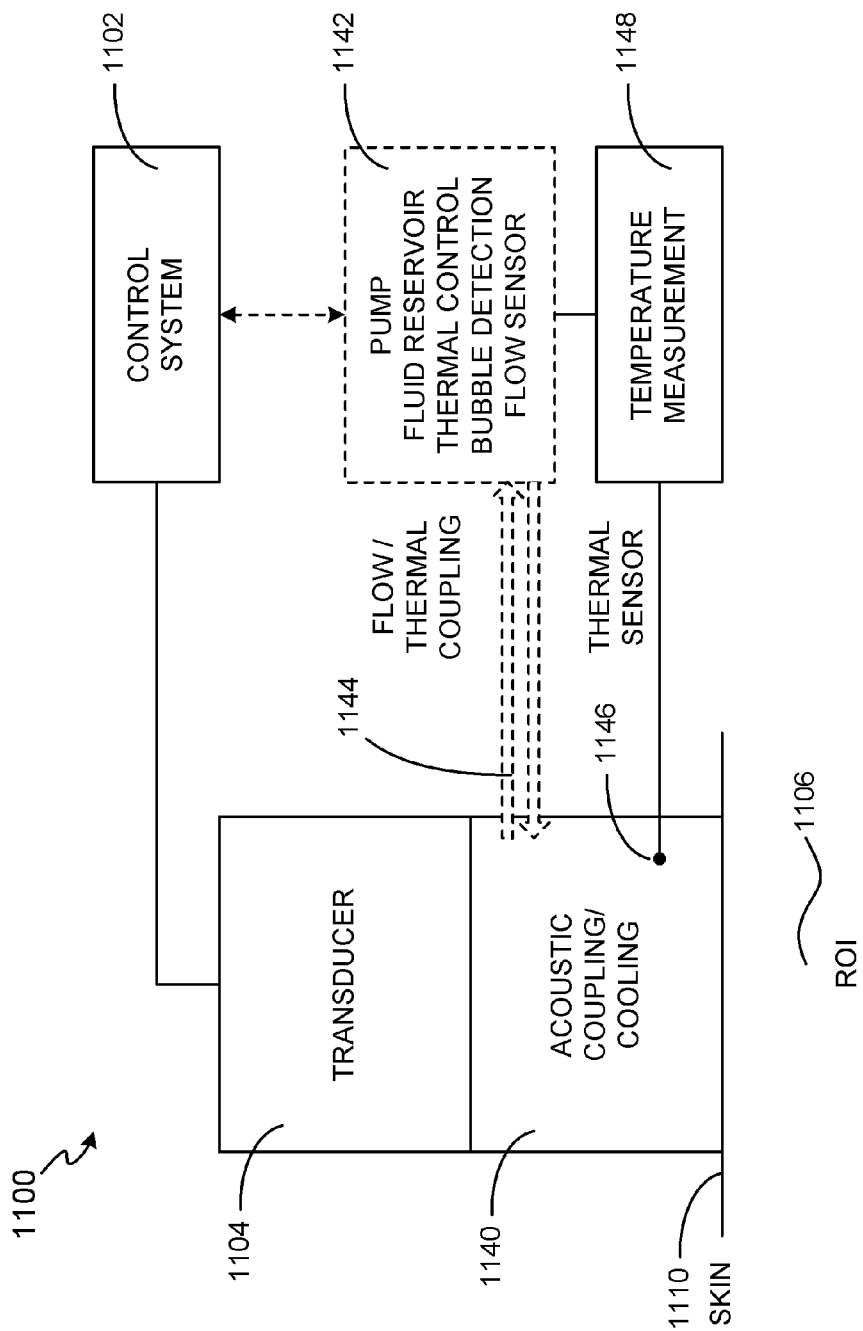
FIG. 11 illustrates a schematic diagram of an acoustic coupling and cooling system in accordance with an exemplary embodiment of the present invention.

In accordance with an exemplary embodiment, with additional reference to FIG. 11, acoustic coupling and cooling 1140 can be provided to acoustically couple energy and imaging signals from transducer probe 1104 to and from the region of interest 1106 and deeper into tissue, to provide thermal control at the probe 1100 to region-of-interest interface (skin) 1110, and to remove potential waste heat from the transducer probe at region 1144. Temperature monitoring can be provided at the coupling interface via a thermal sensor 1146 to provide a mechanism of temperature measurement 1148 and control via control system 1102 and a thermal control system 1142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 1144 and thermal control 1142.

With continued reference to FIG. 4, monitoring and sensing components 408 can comprise various motion and/or position sensors 416, temperature monitoring sensors 418, user control and feedback switches 414 and other like components for facilitating control by control system 300, e.g., to facilitate spatial and/or temporal control through open-loop and closed-loop feedback arrangements that monitor various spatial and temporal characteristics.

Motion mechanism 410 can comprise manual operation, mechanical arrangements, or some combination thereof. For example, a motion mechanism driver 322 can be suitably controlled by control system 300, such as through the use of accelerometers, encoders or other position/orientation devices 416 to determine and enable movement and positions of transducer probe 400. Linear, rotational or variable movement can be facilitated, e.g., those depending on the treatment application and tissue contour surface.

Transducer 404 can comprise one or more transducers configured for treating of sweat glands and targeted regions. Transducer 404 can also comprise one or more transduction elements and/or lenses 412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 404 can comprise any other materials configured for generating radiation and/or acoustical energy. Transducer 404 can also comprise one or more matching layers configured along with the transduction element such as coupled to the piezoelectrically active material. Acoustic matching layers and/or damping may be employed as necessary to achieve the desired electroacoustic response.

In accordance with an exemplary embodiment, the thickness of the transduction element of transducer 404 can be configured to be uniform. That is, a transduction element 412 can be configured to have a thickness that is substantially the same throughout. In accordance with another exemplary embodiment, the thickness of a transduction element 412 can also be configured to be variable. For example, transduction element(s) 412 of transducer 404 can be configured to have a first thickness selected to provide a center operating frequency of approximately 2 kHz to 75 MHz, such as for imaging applications. Transduction element 412 can also be configured with a second thickness selected to provide a center operating frequency of approximately 2 to 50 MHz, and typically between 2 MHz and 25 MHz for therapy application. Transducer 404 can be configured as a single broadband transducer excited with at least two or more frequencies to provide an adequate output for generating a desired response. Transducer 404 can also be configured as two or more individual transducers, wherein each transducer comprises one or more transduction element. The thickness of the transduction elements can be configured to provide center-operating frequencies in a desired treatment range.

Figure 5:
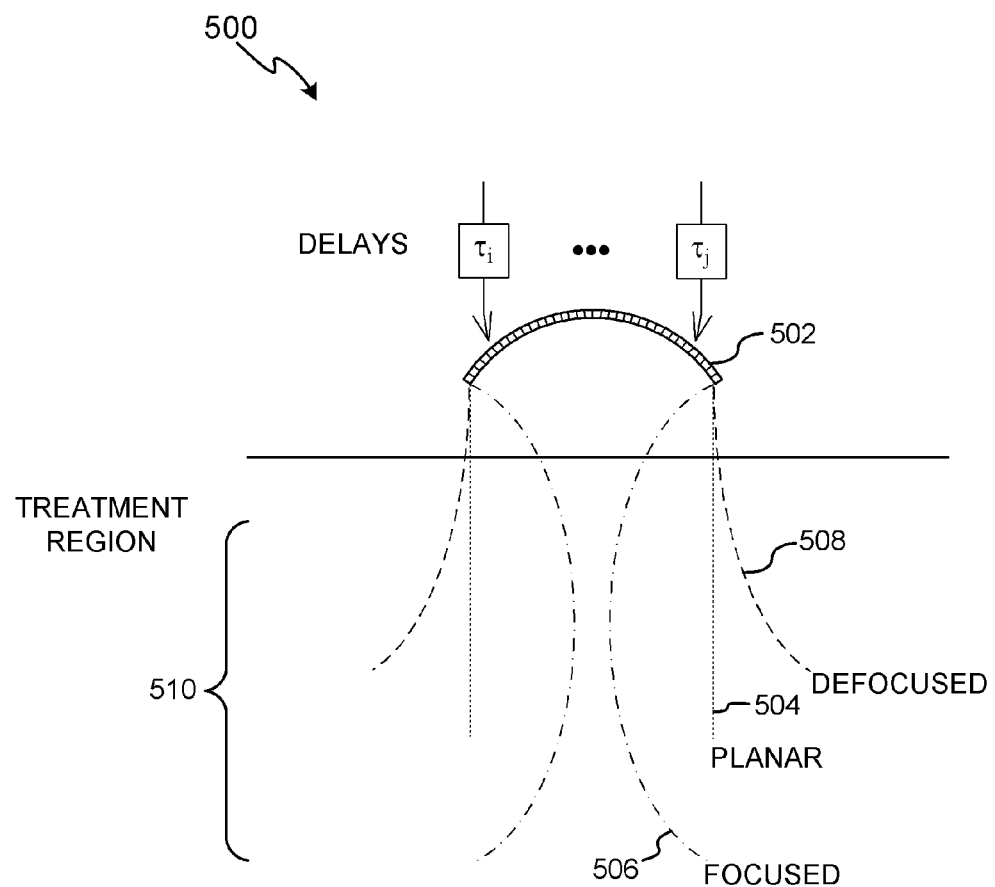
FIG. 5 illustrates a cross-sectional diagram of an exemplary transducer in accordance with an exemplary embodiment of the present invention.

Transducer 404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an exemplary embodiment depicted in FIG. 5, transducer 500 can be configured as an acoustic array 502 to facilitate phase focusing. That is, transducer 500 can be configured as an array of electronic apertures that may be operated by a variety of phases via variable electronic time delays. By the term "operated," the electronic apertures of transducer 500 may be manipulated, driven, used, and/or configured to produce and/or deliver an energy beam corresponding to the phase variation caused by the electronic time delay. For example, these phase variations can be used to deliver defocused beams 508, planar beams 504, and/or focused beams 506, each of which may be used in combination to achieve different physiological effects in a region of interest 510. Transducer 500 may additionally comprise any software and/or other hardware for generating, producing and or driving a phased aperture array with one or more electronic time delays.

Transducer 500 can also be configured to provide focused treatment to one or more regions of interest using various frequencies. In order to provide focused treatment, transducer 500 can be configured with one or more variable depth devices to facilitate treatment. For example, transducer 500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 500 can also be configured to treat one or more additional ROI 510 through the enabling of sub-harmonics or pulse-echo imaging, as disclosed in U.S. patent application Ser. No. 10/944,499, entitled "Method and System for Ultrasound Treatment with a Multi-directional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and or defocus the sound field. For example, with reference to exemplary embodiments depicted in FIGS. 6A and 6B, transducer 600 may also be configured with an electronic focusing array 602 in combination with one or more transduction elements 606 to facilitate increased flexibility in treating ROI 610. Array 602 may be configured in a manner similar to transducer 502. That is, array 602 can be configured as an array of electronic apertures that may be operated by a variety of phases via variable electronic time delays, for example, T1, T2 ... Tj. By the term "operated," the electronic apertures of array 602 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 610.

Transduction elements 606 may be configured to be concave, convex, and/or planar. For example, in an exemplary embodiment depicted in FIG. 6A, transduction elements 606 are configured to be concave in order to provide focused energy for treatment of ROI 610. Additional embodiments are disclosed in U.S. patent application Ser. No. 10/944,500, entitled "Variable Depth Transducer System and Method", and again incorporated herein by reference.

Figure 6A:
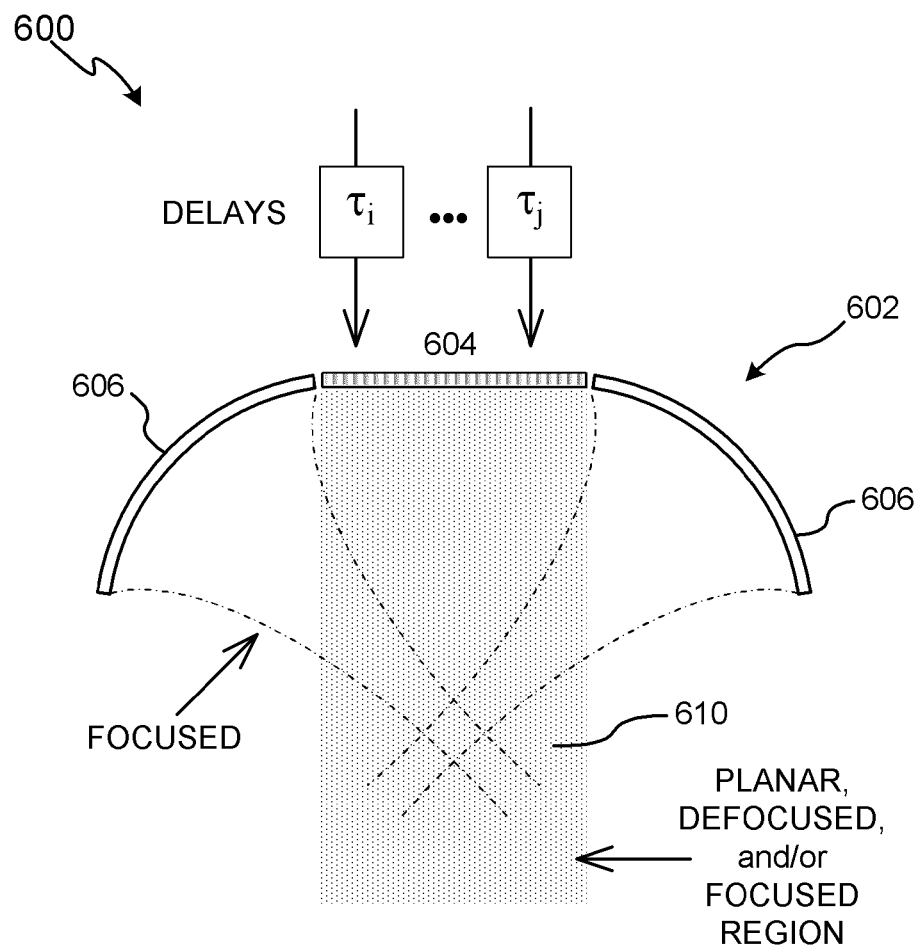
FIGS. 6A and 6B illustrate cross-sectional diagrams of an exemplary transducer in accordance with exemplary embodiments of the present invention.
Figure 6B:
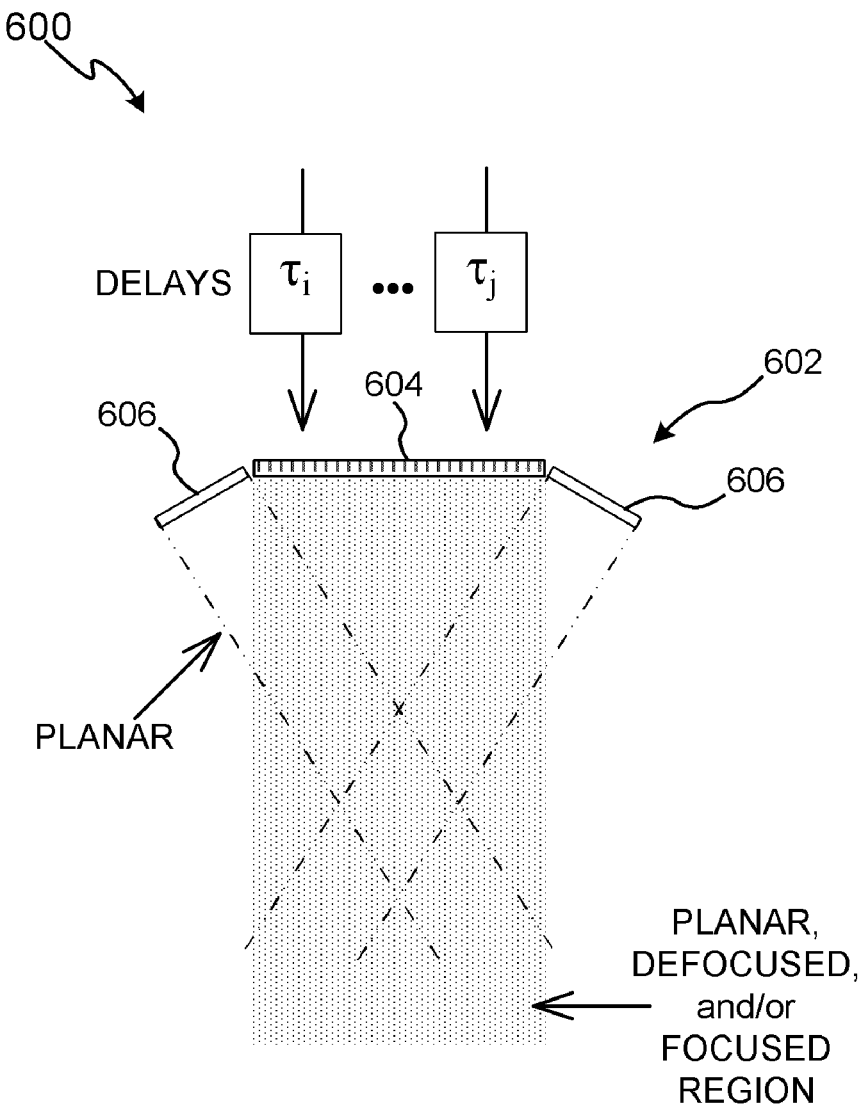

In another exemplary embodiment, depicted in FIG. 6B, transduction elements 606 can be configured to be substantially flat in order to provide substantially uniform energy to ROI 610. While FIGS. 6A and 6B depict exemplary embodiments with transduction elements 604 configured as concave and substantially flat, respectively, transduction elements 604 can be configured to be concave, convex, and/or substantially flat. In addition, transduction elements 604 can be configured to be any combination of concave, convex, and/or substantially flat structures. For example, a first transduction element can be configured to be concave, while a second transduction element can be configured to be substantially flat.

Figure 8A:
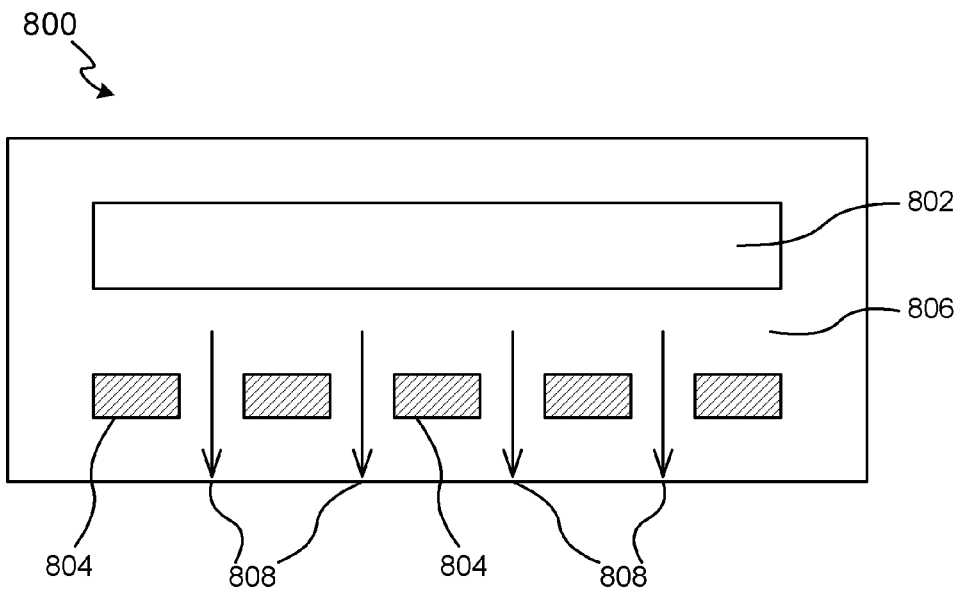
FIGS. 8A and 8B illustrate cross-sectional diagrams of an exemplary transducer in accordance with another exemplary embodiment of the present invention.
Figure 8B:
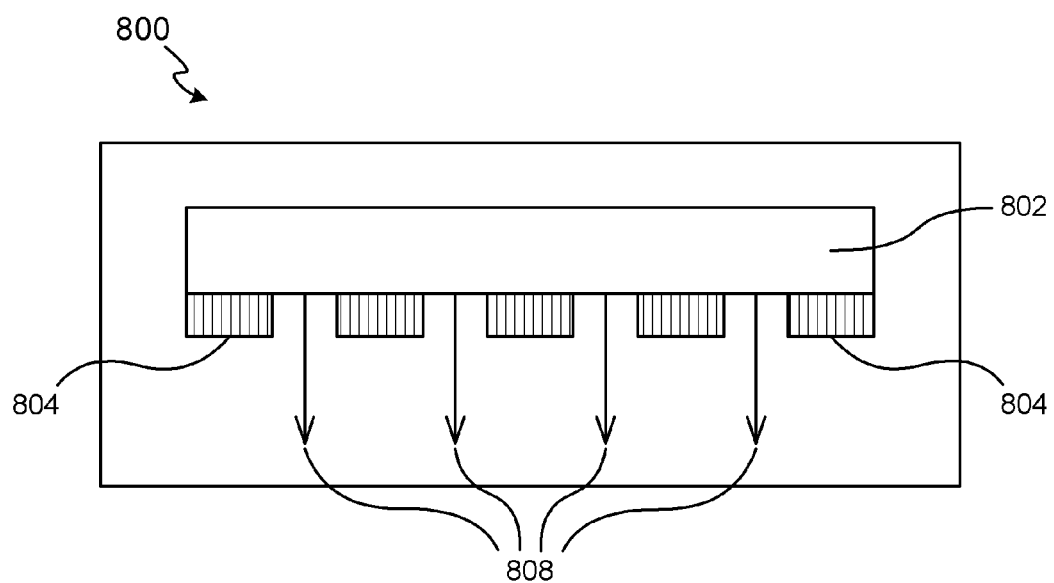

With reference to FIGS. 8A and 8B, transducer 800 can be configured as single-element arrays, wherein a single-element 802, e.g., a transduction element of various structures and materials, can be configured with a plurality of masks 804, such masks comprising ceramic, metal or any other material or structure for masking or altering energy distribution from element 802, creating an array of energy distributions 808. Masks 804 can be coupled directly to element 802 or separated by a standoff 806, such as any suitably solid or liquid material.

Figure 10A:
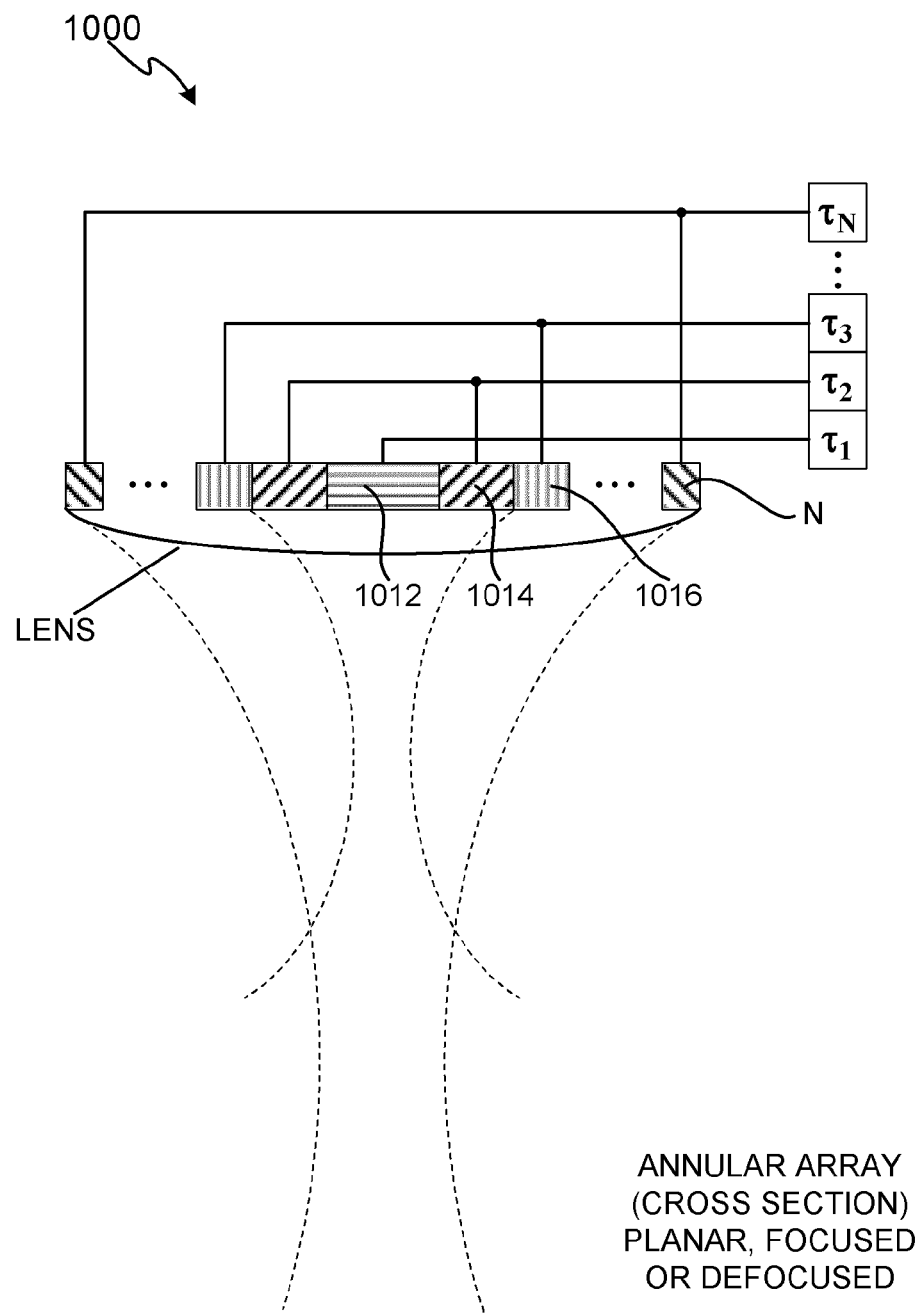
FIGS. 10A-10F illustrate cross-sectional diagrams of exemplary transducers in accordance with other exemplary embodiments of the present invention.
Figure 10B:
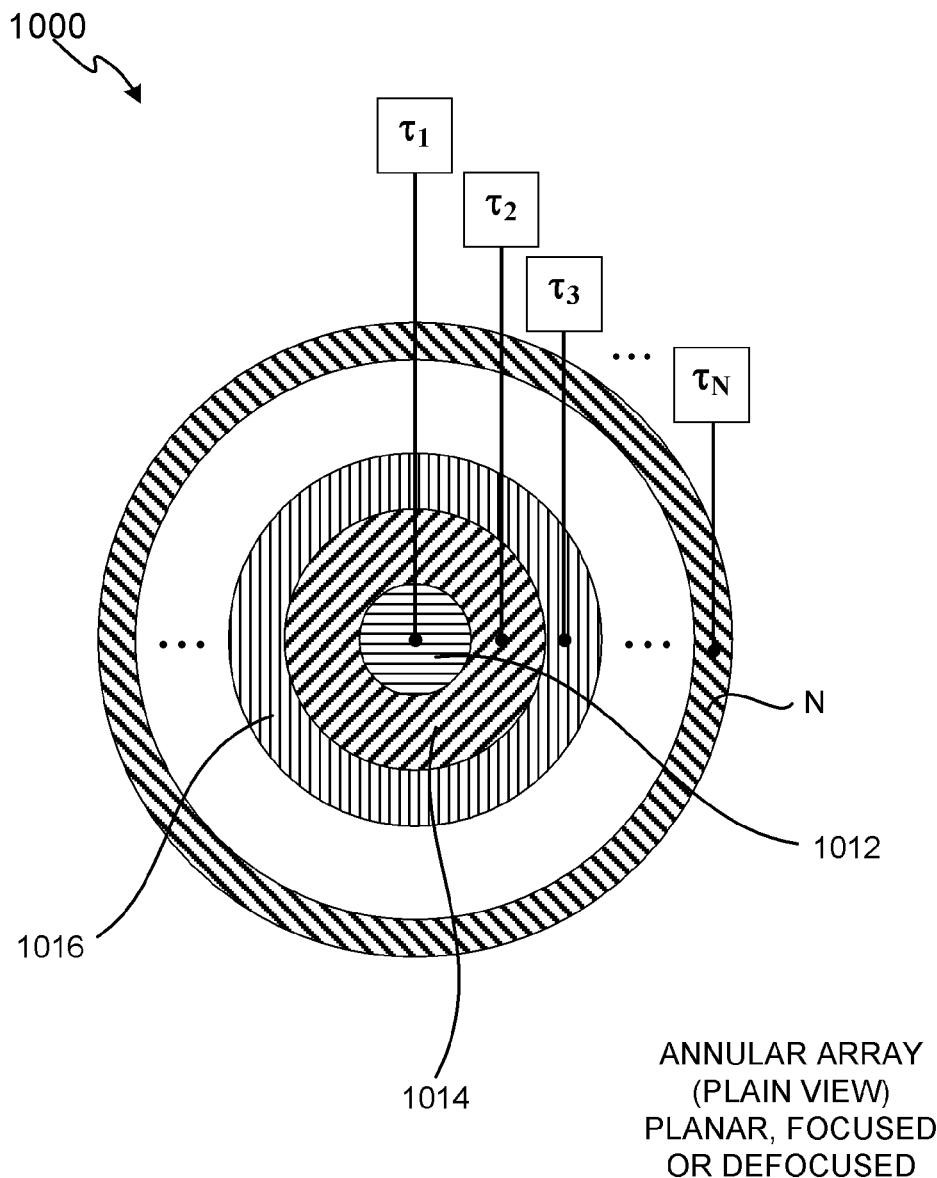
Figure 10C:
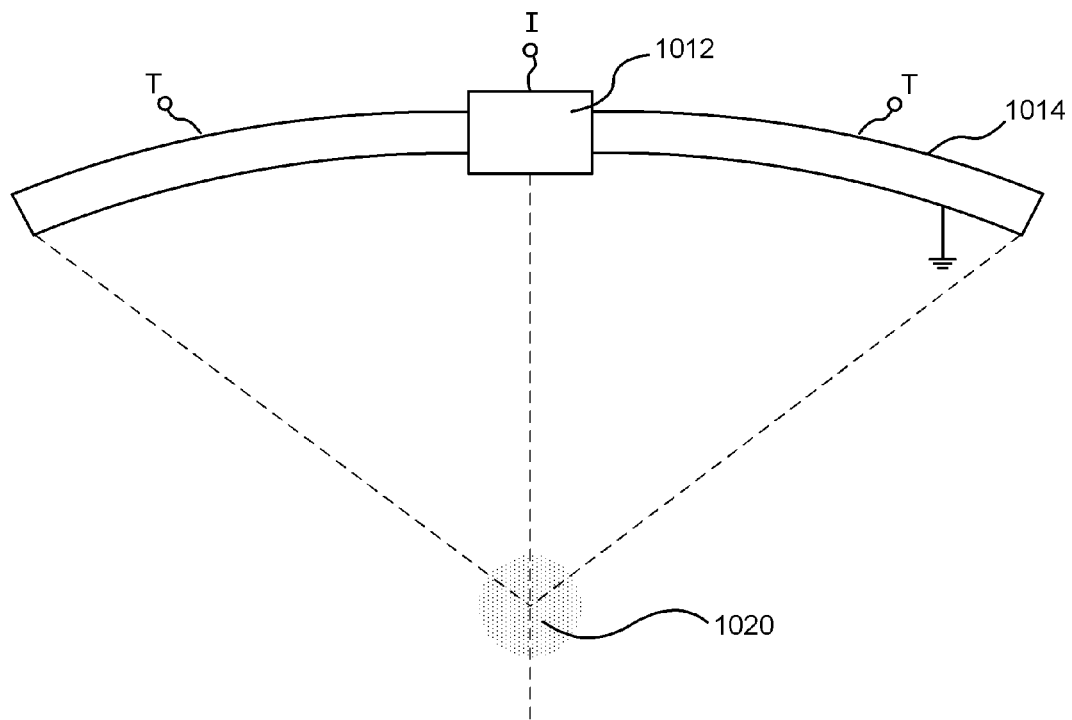
Figure 10D:
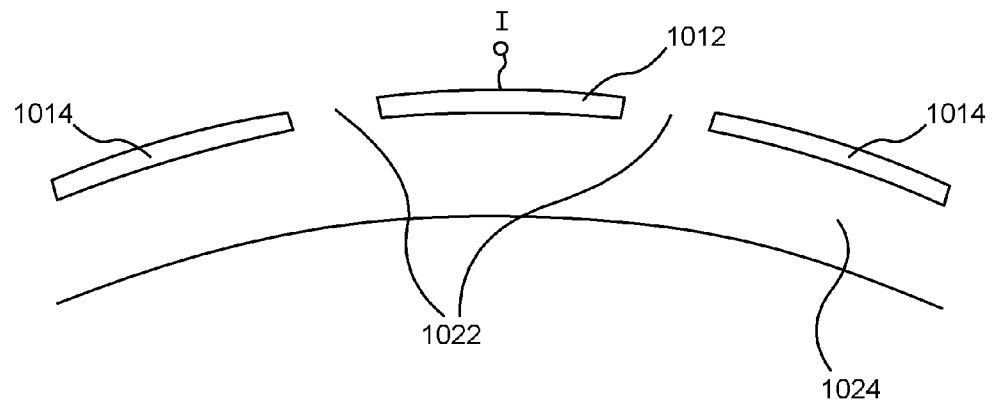
Figure 10E:
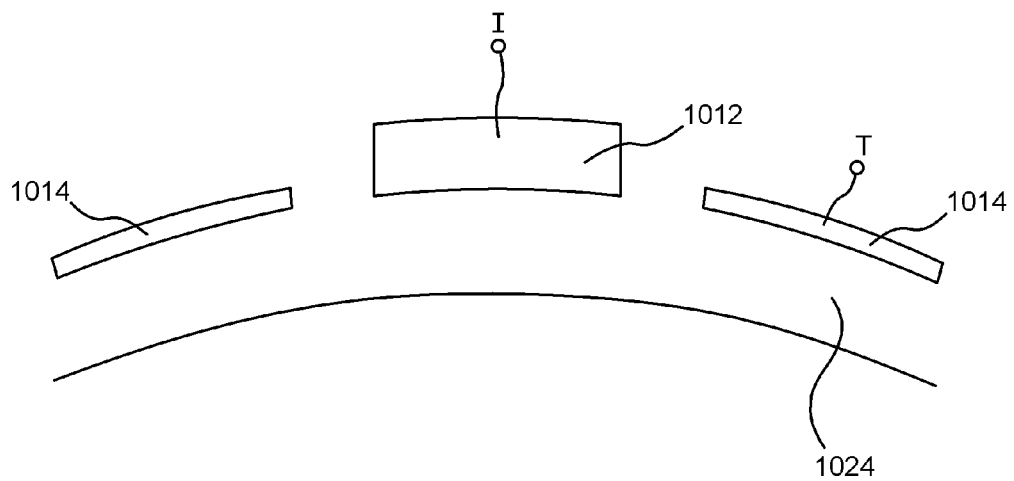

An exemplary transducer 404 can also be configured as an annular array to provide planar, focused and/or defocused acoustical energy. For example, with reference to FIGS. 10A and 10B, in accordance with an exemplary embodiment, an annular array 1000 can comprise a plurality of rings 1012, 1014, 1016 to N. Rings 1012, 1014, 1016 to N can be mechanically and electrically isolated into a set of individual elements, and can create planar, focused, or defocused waves. For example, such waves can be centered on-axis, such as by methods of adjusting corresponding transmit and/or receive delays, $\tau 1, \tau 2, \tau 3 \ldots \tau N$. An electronic focus 1020 can be suitably moved along various depth positions, and can enable variable strength or beam tightness, while an electronic defocus can have varying amounts of defocusing. In accordance with an exemplary embodiment, a lens and/or convex or concave shaped annular array 1000 can also be provided to aid focusing or defocusing such that any time differential delays can be reduced. Movement of annular array 800 in one, two or three-dimensions, or along any path, such as through use of probes and/or any conventional robotic arm mechanisms, may be implemented to scan and/or treat a volume or any corresponding space within a region of interest.

Transducer 404 can also be configured in other annular or non-array configurations for imaging/therapy functions. For example, with reference to FIGS. 10C-10F, a transducer can comprise an imaging element 1012 configured with therapy element(s) 1014. Elements 1012 and 1014 can comprise a single-transduction element, e.g., a combined imaging/transducer element, or separate elements, can be electrically isolated 1022 within the same transduction element or between separate imaging and therapy elements, and/or can comprise standoff 1024 or other matching layers, or any combination thereof. For example, with particular reference to FIG. 10F, a transducer can comprise an imaging element 1012 having a surface 1028 configured for focusing, defocusing or planar energy distribution, with therapy elements 1014 including a stepped-configuration lens configured for focusing, defocusing, or planar energy distribution.

In accordance with various exemplary embodiments of the present invention, transducer 404 may be configured to provide one, two and/or three-dimensional treatment applications for focusing acoustic energy to one or more regions of interest. For example, as discussed above, transducer 404 can be suitably diced to form a one-dimensional array, e.g., transducer 602 comprising a single array of sub-transduction elements.

Figure 9:
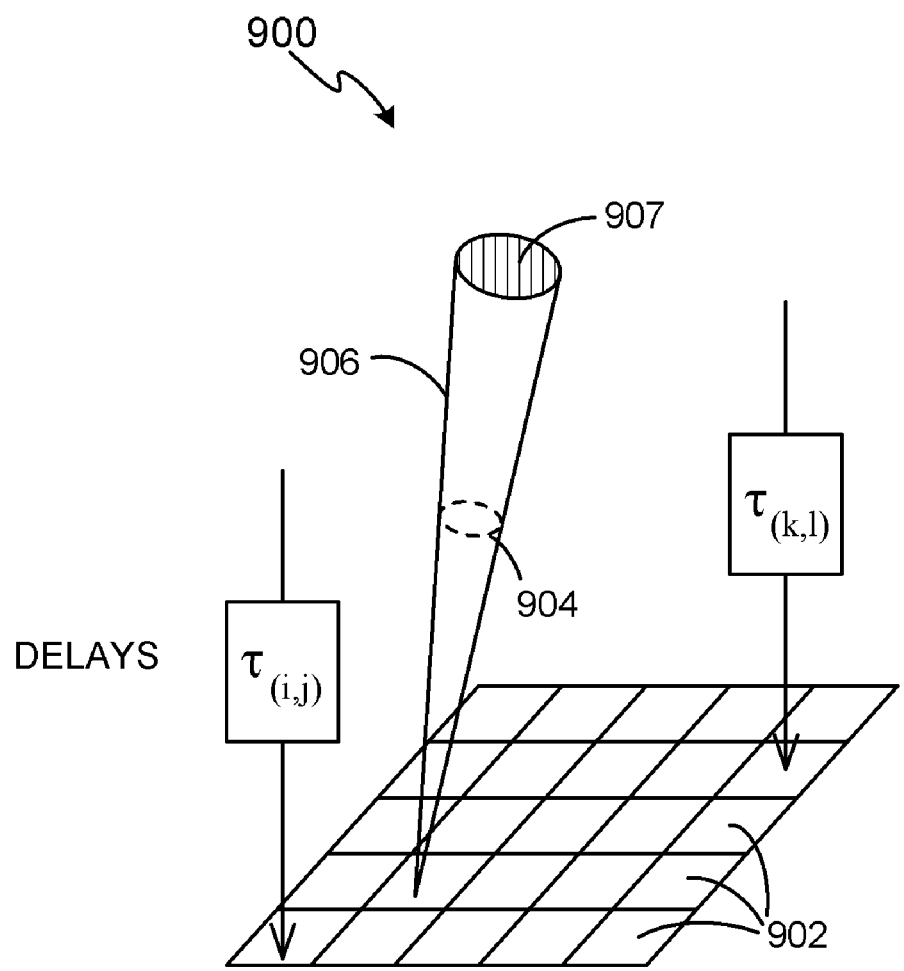
FIG. 9 illustrates an exemplary transducer configured as a two-dimensional array for ultrasound treatment in accordance with an exemplary embodiment of the present invention.

In accordance with another exemplary embodiment, transducer 404 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904, 907 of the treatment region. As a result, the two-dimensional array 900 can provide a two-dimensional slicing of the image place of a treatment region, thus providing two-dimensional treatment.

In accordance with another exemplary embodiment, transducer 404 may be suitably configured to provide three-dimensional treatment. For example, to provide-three dimensional treatment of a region of interest, with reference again to FIG. 1, a three-dimensional system can comprise a transducer within probe 104 configured with an adaptive algorithm, such as, for example, one utilizing three-dimensional graphic software, contained in a control system, such as control system 102. The adaptive algorithm is suitably configured to receive two-dimensional imaging, temperature and/or treatment or other tissue parameter information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

In accordance with other exemplary embodiments, rather than utilizing an adaptive algorithm, such as three-dimensional software, to provide three-dimensional imaging and/or temperature information, an exemplary three-dimensional system can comprise a single transducer 404 configured within a probe arrangement to operate from various rotational and/or translational positions relative to a target region.

Figure 7:
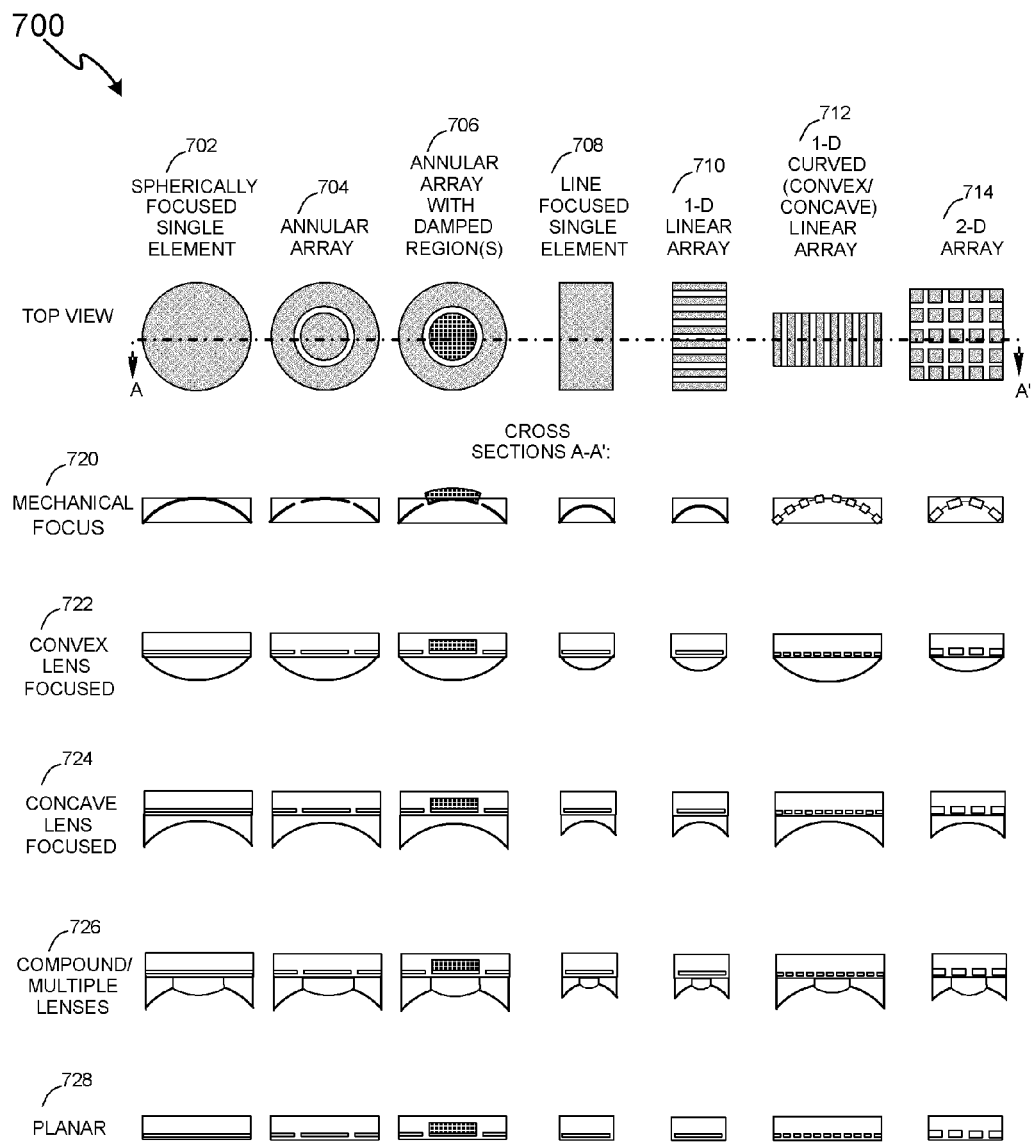
FIG. 7 illustrates exemplary transducer configurations for ultrasound treatment in accordance with various exemplary embodiments of the present invention.
Figure 10F:
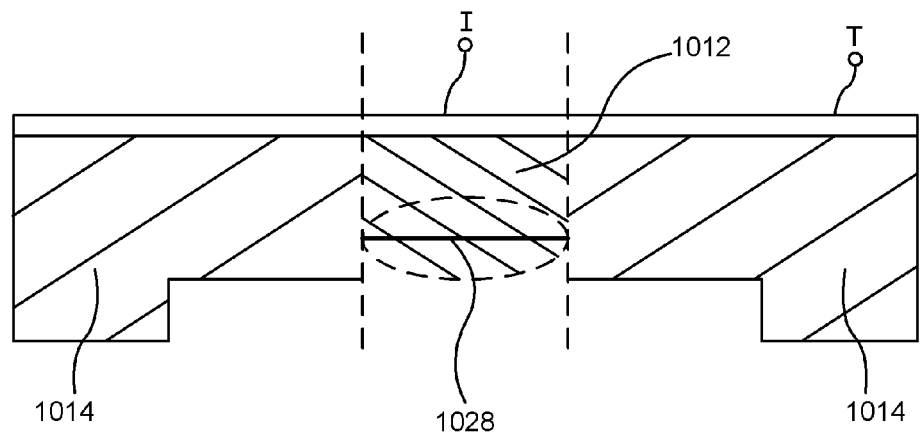

To further illustrate the various structures for transducer 404, with reference to FIG. 7, ultrasound therapy transducer 700 can be configured for a single focus, an array of foci, a locus of foci, a line focus, and/or diffraction patterns. Transducer 700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 702, annular arrays 704, annular arrays with damped regions 706, line focused single elements 708, 1-D linear arrays 710, 1-D curvilinear arrays in concave or convex form, with or without elevation focusing 712, 2-D arrays 714, and 3-D spatial arrangements of transducers may be used to perform therapy and/or imaging and acoustic monitoring functions. For any transducer configuration, focusing and/or defocusing may be in one plane or two planes via mechanical focus 720, convex lens 722, concave lens 724, compound or multiple lenses 726, planar form 728, or stepped form, such as illustrated in FIG. 10F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIG. 10C-10F.

Moreover, such transduction elements 700 may comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. Transduction elements 700 may also comprise one or more matching layers configured along with the piezoelectrically active material. In addition to or instead of piezoelectrically active material, transduction elements 700 can comprise any other materials configured for generating radiation and/or acoustical energy. A means of transferring energy to and from the transducer to the region of interest is provided.

Figure 12:
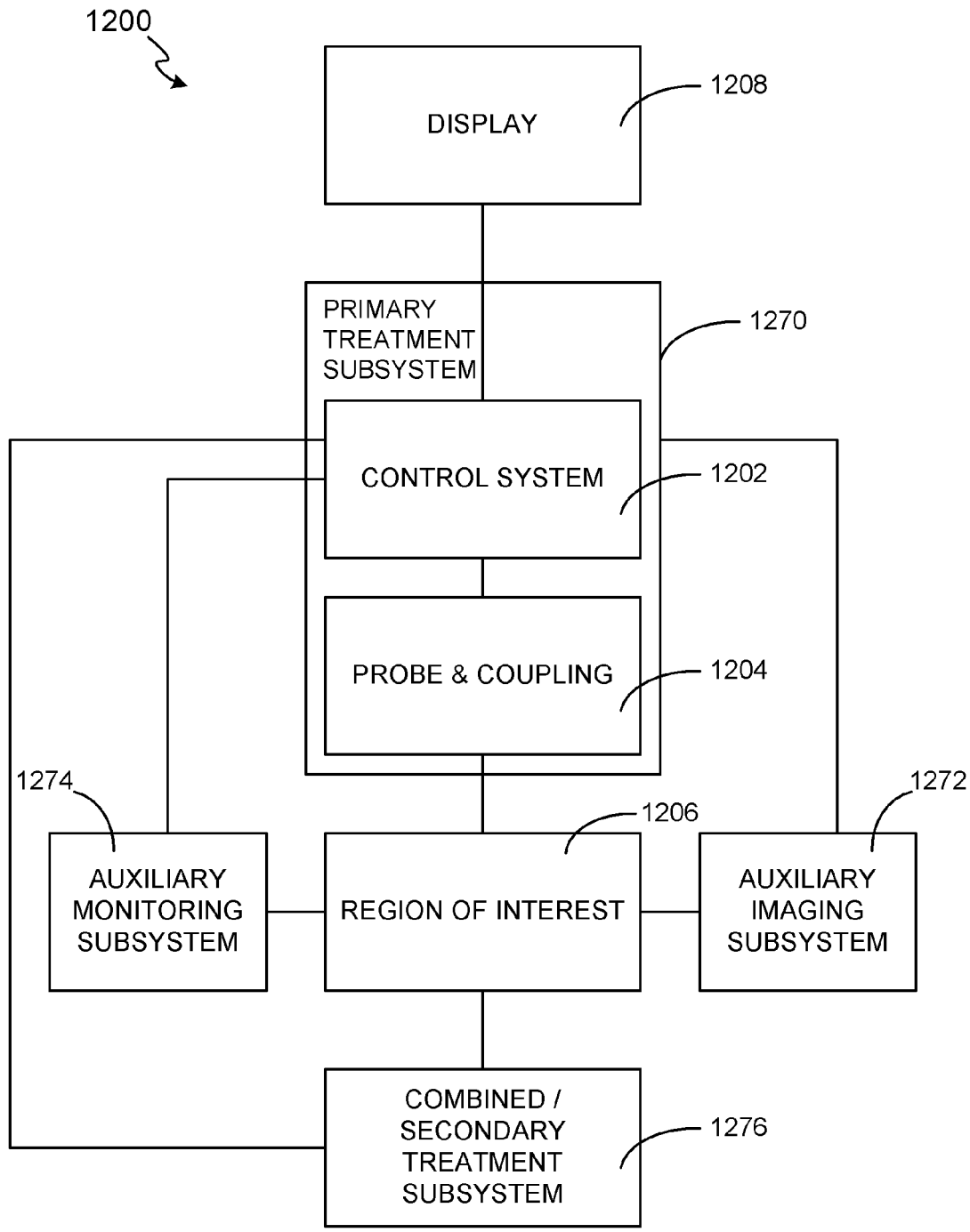
FIG. 12 illustrates a block diagram of an ultrasound treatment system combined with additional subsystems and methods of treatment monitoring and/or treatment imaging as well as a secondary treatment subsystem in accordance with an exemplary embodiment of the present invention.

In accordance with another exemplary embodiment, with reference to FIG. 12, an exemplary treatment system 200 can be configured with and/or combined with various auxiliary systems to provide additional functions. For example, an exemplary treatment system 1200 for treatment of sweat glands can comprise a control system 1206, a probe 1204, and a display 1208. For example, an exemplary treatment system 1200 for treatment of sweat glands can further comprise an auxiliary imaging subsystem 1272 and/or auxiliary monitoring modality 1274 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of the region-of-interest 1202, including imaging/monitoring enhancements. Such imaging/monitoring enhancement for ultrasound imaging via probe 1204 and control system 1206 can comprise M-mode, persistence, filtering, color, Doppler, and harmonic imaging among others; furthermore an ultrasound treatment system 1270, as a primary source of treatment, may be combined with a secondary treatment subsystem 1276, including radio frequency (RF), intense pulsed light (IPL), laser, infrared laser, microwave, or any other suitable energy source.

Figure 13:
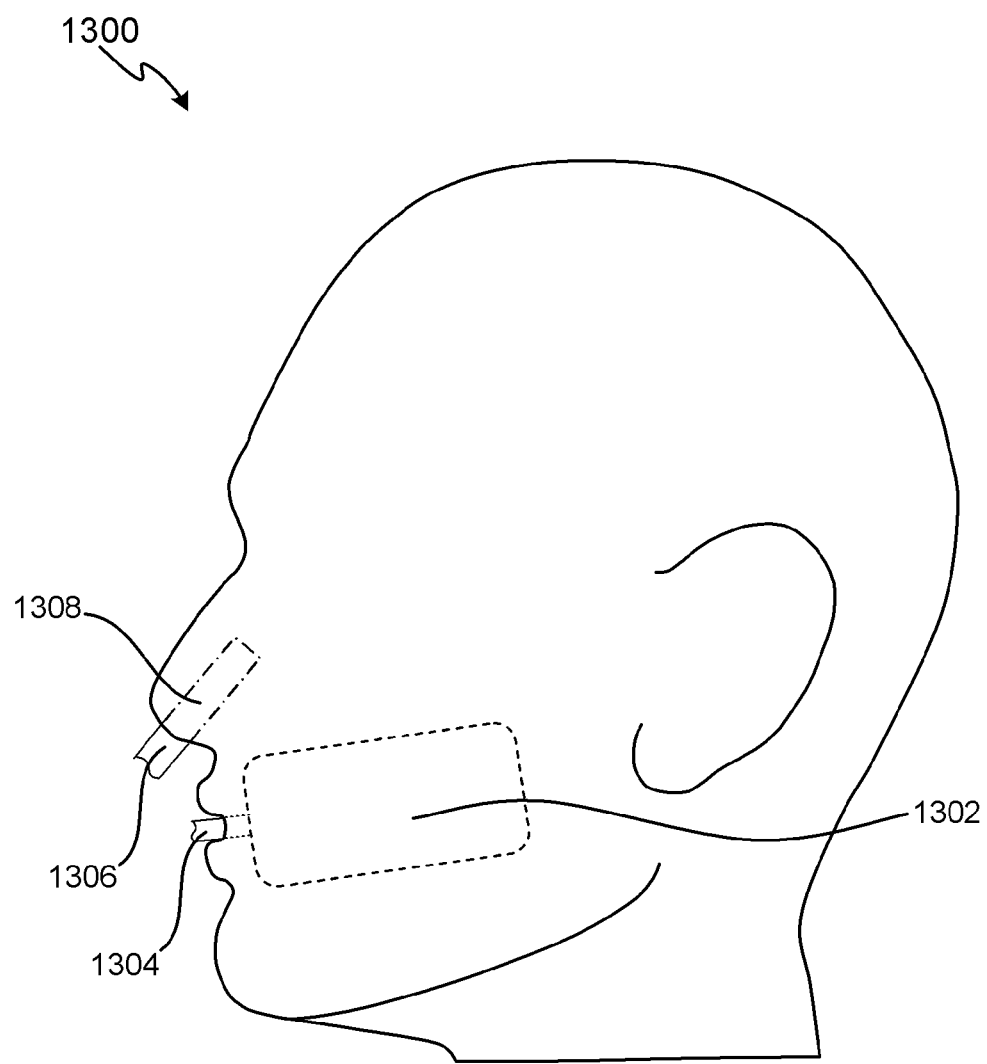
FIG. 13 illustrates a schematic diagram with imaging, therapy, or monitoring being provided with one or more active or passive oral inserts in accordance with an exemplary embodiment of the present invention.

In accordance with another exemplary embodiment, with reference to FIG. 13, treatment composed of imaging, monitoring, and/or therapy to a region of interest 1302 and/or 1308 may be aided, augmented, and/or delivered with passive or active devices 1304 and/or 1306 within the oral and/or nasal cavity, respectively. For example, if passive or active device 1304 and/or 1306 are second transducers or acoustic reflectors acoustically coupled to the mucous membranes it is possible to obtain through transmission, tomographic, or round-trip acoustic waves which are useful for treatment monitoring, such as in measuring acoustic speed of sound and attenuation, which are temperature dependent; furthermore such transducers could be used to treat and/or image. In addition an active, passive, or active/passive object 1304 and/ or 1306 may be used to flatten the skin, and/or may be used as an imaging grid, marker, or beacon, to aid determination of position. A passive or active device 1304 and/or 1306 may also be used to aid cooling or temperature control. Natural air in the oral cavity and/or nasal cavity may also be used as passive device 1304 and/or 1306 whereby it may be utilized to as an acoustic reflector to aid thickness measurement and monitoring function.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a system as described herein are merely indicative of exemplary applications for the invention. For example, the principles, features and methods discussed may be applied to any medical application. Further, various aspects of the present invention may be suitably applied to other applications, such as other medical or industrial applications.

What is claimed is:

1. A non-invasive method for treating sweat glands to reduce sweat, said method comprising:
    acoustically coupling an ultrasound probe to a skin surface,
    wherein said ultrasound probe comprises an ultrasound imaging element and an ultrasound therapy element;
    using the ultrasound imaging element to image a region of interest under said skin surface, wherein the region of interest comprises a sweat gland;
    wherein the sweat gland is displayed on a display system, said display system being electronically connected to said ultrasound imaging element;
    using a motion mechanism to move the ultrasound therapy element to create a plurality of thermal lesions to thermally ablate said sweat gland in said region of interest to reduce sweat,
    wherein said ultrasound therapy element is configured to deliver ultrasound energy at a depth of about 1 to about 7 mm below the skin surface.

2. The method of claim 1, wherein said using the ultrasound therapy element comprises destroying said at least one sweat gland within a specified treatment depth identified through localization of said sweat gland.

3. The method of claim 1, wherein said using the ultrasound therapy element comprises adjustable control of spatial parameters and temporal parameters of said transducer probe to generate conformal lesions of specifically targeted shapes, sizes or orientations.

4. The method of claim 1, wherein the motion mechanism is coupled to the ultrasound therapy element within the ultrasound probe.

5. The method according to claim 1, wherein the step of creating said plurality of thermal lesions comprises producing a discrete locus of spaced conformal lesions based on adjustable control of spatial parameters and temporal parameters.

6. The method according to claim 1, wherein the step of creating said plurality of thermal lesions comprises producing a one-, two- or three-dimensional matrix of spaced lesions to reduce sweat.

7. The method of claim 1, further comprising:
    monitoring of said sweat gland for further planning, assessing of results, or providing feedback.

8. The method of claim 1, further comprising monitoring a temperature of said region of interest.

9. The method according to claim 1, wherein said imaging comprises generating three-dimensional imaging information and said delivering ultrasound energy comprises treating a three-dimensional treatment region.

10. The method according to claim 1, wherein the skin surface is any one selected from the group consisting of a face, head, armpit, palm, and sole.

11. A method for providing treatment for reducing sweat gland activity, said method comprising:
    targeting therapeutic acoustic waves, via an ultrasound treatment element housed within an ultrasound probe, through a skin surface to treat a sweat gland under said skin surface;
    moving an automated motion mechanism for controllably creating a plurality of thermal lesions along a line at a depth of about 1 to about 7 mm below the skin surface,
    wherein the automated motion mechanism comprises at least one of the group consisting of an accelerometer, encoder and a position/orientation device;
    wherein the automated motion mechanism is controlled by a control system in communication with the ultrasound probe;
    wherein the plurality of thermal lesions reduces activity in the sweat gland to reduce sweat production by said sweat gland.

12. The method of treating sweat glands to reduce sweat according to claim 11, wherein the skin surface is any one selected from the group consisting of a face, head, armpit, palm, and sole.

13. A method for reducing sweat, said method comprising:
    coupling an ultrasound probe to a skin surface proximate to at least one sweat gland;
    wherein said ultrasound probe comprises an ultrasound therapy element;
    selecting an ultrasound probe configuration based on at least one of a spatial parameter and a temporal parameter;
    verifying said at least one of a spatial parameter and a temporal parameter of said probe; and
    using a motion mechanism to move the ultrasound therapy element to create a plurality of thermal lesions to reduce sweat production in said at least one sweat gland.

14. The method of claim 13, further comprising using an ultrasound imaging element in said ultrasound probe to image a region of interest under said skin surface comprising said at least one sweat gland.

15. The method of claim 13, wherein said using the motion mechanism to move the ultrasound therapy element comprises destroying said at least one sweat gland within a specified treatment depth identified through localization of said at least one sweat gland.

16. The method of claim 13, wherein said using the motion mechanism to move the ultrasound therapy element comprises controlling spatial parameters and temporal parameters of said probe to generate conformal lesions of specifically targeted shapes, sizes and orientations.

17. The method of claim 13, wherein said using the motion mechanism to move the ultrasound therapy element comprises producing a matrix of spaced treatment spots comprising at least one of a two-dimensional and three-dimensional matrix of lesions along a scanned pattern created by scanning of said probe, wherein said producing said matrix of spaced treatment spots comprises producing a discrete locus of spaced lesions based on adjustable control of spatial parameters and temporal parameters.

18. The method according to claim 13, further comprising shocking the sweat gland in to a state of reduced activity via any one in the group consisting of acoustic cavitation, acoustic streaming, inter-cellular shear effects, and cell resonant effects.

19. The method according to claim 13, further comprising cooling through any tissue regions between and including skin and said at least one sweat gland to facilitate treatment.

20. The method according to claim 13, further comprising administering a pharmaceutical agent to the sweat gland to further reduce sweat production.

* * * * *